(12) United States Patent
Jordan et al.

(10) Patent No.: US 10,806,948 B2
(45) Date of Patent: *Oct. 20, 2020

(54) ONLINE ANGLE SELECTION IN ROTATIONAL IMAGING AND TRACKING SYSTEMS

(71) Applicant: Accuray Incorporated, Sunnyvale, CA (US)

(72) Inventors: Petr Jordan, Redwood City, CA (US); Andriy Myronenko, San Mateo, CA (US); Calvin Maurer, San Jose, CA (US); Eric Schnarr, McFarland, WI (US); Rob O'Connell, Madison, WI (US)

(73) Assignee: Accuray Incorporated, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/595,194

(22) Filed: Oct. 7, 2019

(65) Prior Publication Data
US 2020/0047000 A1 Feb. 13, 2020

Related U.S. Application Data

(60) Continuation of application No. 16/427,719, filed on May 31, 2019, now Pat. No. 10,456,599, which is a
(Continued)

(51) Int. Cl.
*A61N 5/10* (2006.01)
*A61B 6/00* (2006.01)

(52) U.S. Cl.
CPC ............ *A61N 5/107* (2013.01); *A61B 6/4014* (2013.01); *A61N 5/103* (2013.01); *A61N 5/1037* (2013.01);
(Continued)

(58) Field of Classification Search
CPC ....................................................... A61N 5/10
See application file for complete search history.

(56) References Cited

U.S. PATENT DOCUMENTS 8,379,794 B2 * 2/2013 Poulsen .................. A61B 6/12
378/20
8,818,105 B2 8/2014 Myronenko et al.
(Continued)

FOREIGN PATENT DOCUMENTS

WO 2007124760 A1 11/2007

OTHER PUBLICATIONS

International Search Report and Written Opinion of the ISA/EP in PCT/US2017/048674 dated Nov. 8, 2017; 10 pages.

*Primary Examiner* — Thomas R Artman
(74) *Attorney, Agent, or Firm* — Womble Bond Dickinson (US) LLP

(57) ABSTRACT

A radiation therapy apparatus determines a set of angles that have a tracking quality metric value that satisfies a tracking quality metric criterion. During an alignment phase or a treatment phase for a treatment stage of a target by the radiation therapy apparatus, the radiation therapy apparatus performs selects at least a first angle and a second angle from the set of angles for a first rotation of the gantry. The radiation therapy apparatus generates, using an imaging device mounted to the gantry, a first tracking image of the target from the first angle during the first rotation of the gantry. The radiation therapy apparatus generates, using the imaging device, a second tracking image of the target from the second angle during the first rotation of the gantry. The radiation therapy apparatus performs the target tracking based on the first tracking image and the second tracking image.

9 Claims, 19 Drawing Sheets

Related U.S. Application Data division of application No. 15/250,582, filed on Aug. 29, 2016, now Pat. No. 10,342,996.

(52) U.S. Cl.
CPC ......... *A61N 5/1039* (2013.01); *A61N 5/1049* (2013.01); *A61N 5/1081* (2013.01); *A61N 5/1083* (2013.01); *A61N 2005/1061* (2013.01); *A61N 2005/1062* (2013.01); *A61N 2005/1074* (2013.01)

(56) References Cited

U.S. PATENT DOCUMENTS

| | | |
|---|---|---|
| 8,917,813 B2 | 12/2014 | Maurer |
| 8,934,605 B2 | 1/2015 | Maurer et al. |
| 9,327,141 B2 | 5/2016 | Maurer et al. |
| 9,387,347 B2 | 7/2016 | Maurer |
| 9,700,740 B2 | 7/2017 | Maurer |
| 10,350,438 B2 * | 7/2019 | Brooks .................. G06N 20/00 |
| 2010/0172469 A1 * | 7/2010 | Poulsen .................. A61B 6/12 |
| | | 378/20 |
| 2011/0210261 A1 | 9/2011 | Maurer |
| 2011/0211665 A1 | 9/2011 | Maurer et al. |
| 2014/0275705 A1 | 9/2014 | Virshup et al. |
| 2015/0073256 A1 | 3/2015 | Maurer |
| 2015/0131774 A1 | 5/2015 | Maurer et al. |
| 2016/0199666 A1 | 7/2016 | Maurer et al. |
| 2016/0303400 A1 | 10/2016 | Maurer |
| 2018/0050222 A1 * | 2/2018 | Feain ....................... A61B 6/50 |
| 2018/0056090 A1 | 3/2018 | Jordan et al. |
| 2018/0056091 A1 | 3/2018 | Jordan et al. |
| 2018/0178037 A1 | 6/2018 | Maurer et al. |
| 2018/0193674 A1 * | 7/2018 | Brooks .................. G16H 30/40 |

* cited by examiner

ONLINE ANGLE SELECTION IN ROTATIONAL IMAGING AND TRACKING SYSTEMS

REFERENCE TO RELATED APPLICATION

This application is a continuation of U.S. application Ser. No. 16/427,719, filed May 31, 2019, which is a divisional of U.S. application Ser. No. 15/250,582, filed Aug. 29, 2016 (now U.S. Pat. No. 10,341,996, issued Jul. 9, 2019), the entire contents of which are hereby incorporated by reference.

FIELD

This patent specification relates to rotational imaging and tracking systems, and in particular to angle selection for rotational imaging and tracking systems.

BACKGROUND

Pathological anatomies such as tumors and lesions can be treated with an invasive procedure, such as surgery, which can be harmful and full of risks for the patient. A non-invasive method to treat a pathological anatomy (e.g., tumor, lesion, vascular malformation, nerve disorder, etc.) is external beam radiation therapy, which typically uses a radiation treatment source (e.g., a linear accelerator (LINAC)) to generate radiation beams such as x-rays. In one type of external beam radiation therapy, a radiation treatment source (also referred to herein as a therapeutic radiation source) directs a sequence of x-ray beams at a tumor site from multiple angles, with the patient positioned so the tumor is at the center of rotation (isocenter) of the beam. As the angle of the therapeutic radiation source changes, every beam passes through the tumor site, but passes through a different area of healthy tissue on its way to and from the tumor. As a result, the cumulative radiation dose at the tumor is high and that to healthy tissue is relatively low.

The term "radiosurgery" refers to a procedure in which radiation is applied to a target region at doses sufficient to treat a pathology in fewer treatment stages (also known as treatment fractions or simply fractions) than with delivery of lower doses per fraction in a larger number of treatment stages. Radiosurgery is typically characterized, as distinguished from radiotherapy, by relatively high radiation doses per fraction or treatment stage (e.g., 500-2000 centiGray), extended treatment times per fraction (e.g., 30-60 minutes per treatment), and hypo-fractionation (e.g., one to five fractions). Radiotherapy is typically characterized by a low dose per fraction or treatment stage (e.g., 100-200 centiGray), shorter fraction times (e.g., 10 to 30 minutes per treatment) and hyper-fractionation (e.g., 30 to 45 fractions). For convenience, the term "radiation treatment" is used herein to mean radiosurgery and/or radiotherapy (also referred to as x-ray therapy and radiation therapy) unless otherwise noted.

Image-guided radiation therapy (IGRT) systems include gantry-based systems and robotic arm-based systems. In gantry-based systems, a gantry rotates the therapeutic radiation source around an axis passing through the isocenter. Gantry-based systems include C-arm gantries, in which the therapeutic radiation source is mounted, in a cantilever-like manner, over and rotates about the axis passing through the isocenter. Gantry-based systems further include ring gantries having generally toroidal shapes in which the patient's body extends through a bore of the ring/toroid, and the therapeutic radiation source is mounted on the perimeter of the ring and rotates about the axis passing through the isocenter. Robotic arm-based systems include a robotic arm to which the therapeutic radiation source is mounted.

Associated with each radiation therapy system is an imaging system to provide in-treatment images (referred to herein as tracking images) that are used to set up and, in some examples, guide the radiation delivery procedure and track in-treatment target motion. Portal imaging systems place a detector opposite the therapeutic radiation source to image the patient for setup and in-treatment images, while other approaches utilize distinct, independent image radiation source(s) and detector(s) for the patient set-up and in-treatment images. Tracking images generated at some angles may be better suited to target tracking than tracking images generated at other angles. However, it can be difficult to determine which angles will produce the optimal target tracking performance.

DETAILED DESCRIPTION

Figure 1:
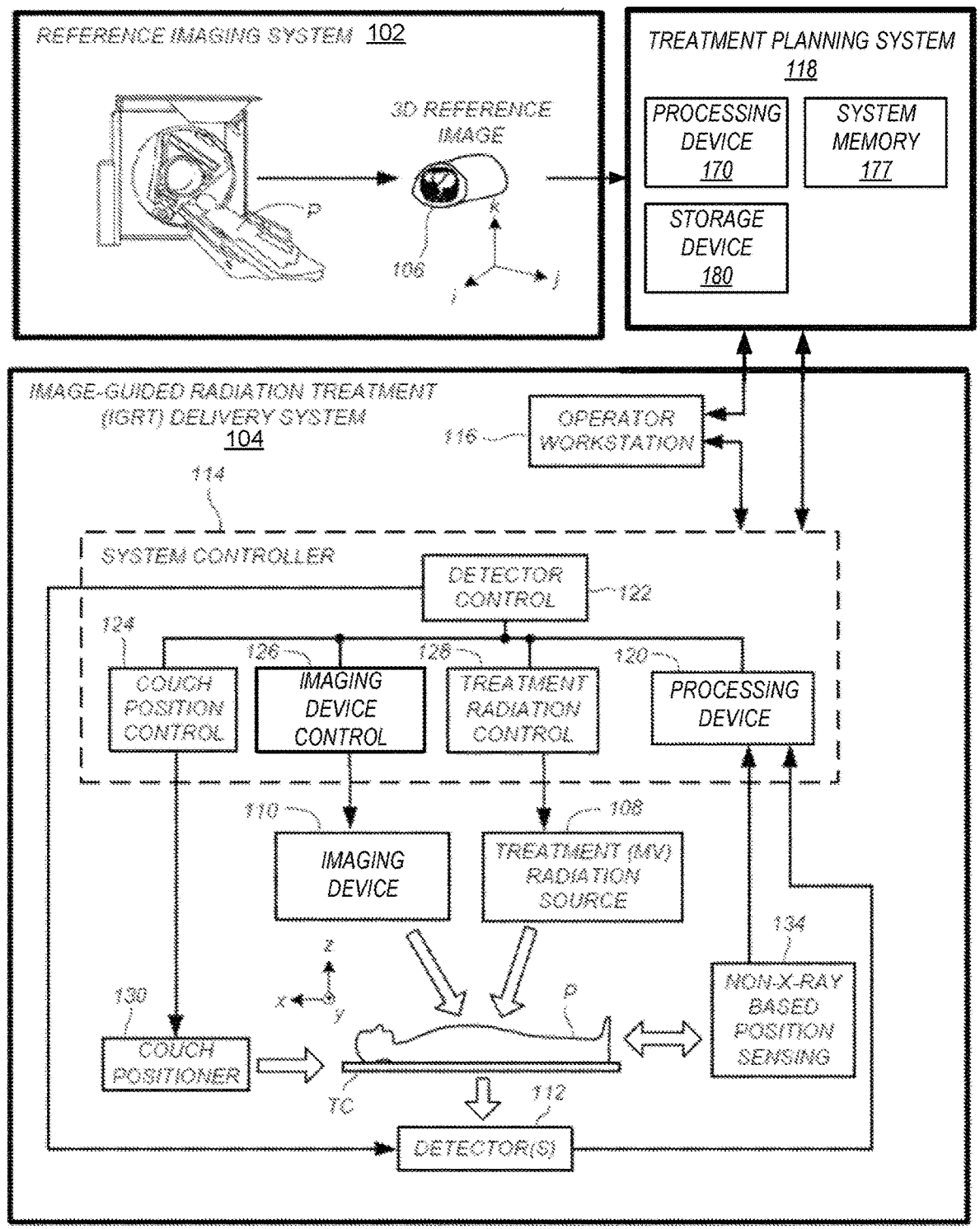
FIG. 1 illustrates a radiation treatment environment according to embodiments.

Embodiments of the present invention are directed to methods and systems for selecting angles (referred to as imaging angles) to be used by an imaging system to generate tracking images of a target during a treatment stage. Imaging systems with movable imaging devices may be able to generate tracking images from many different angles. However, some angles may be superior to other angles for target tracking purposes. For example, at some imaging angles a target that is to be treated may not be discoverable and/or may be indistinguishable from other structures. At other imaging angles, target tracking algorithms may incorrectly identify a non-target structure as the target. Selection of optimal angles for generating tracking images is non-trivial, and can have important consequences in a treatment stage. Image angle selection can be of particular importance for image-guided radiation therapy.

In one embodiment, a processing device determines a plurality of angles from which tracking images can be generated by an imaging device. The processing device generates a plurality of projections of a three-dimensional treatment planning image of a patient, such as a computer tomography (CT) scan of the patient, a magnetic resonance imaging (MRI) scan of the patient, or a three-dimensional image of the patient based on another three-dimensional imaging modality. The three-dimensional treatment planning image includes a delineated target, wherein each projection of the plurality of projections has an angle that corresponds to one of the plurality of angles from which the tracking images can be taken. The processing device determines, for each angle of the plurality of angles, a value of a tracking quality metric for tracking the target based on an analysis of a projection generated at that angle. The processing device selects a subset of the plurality of angles that have a tracking quality metric value that satisfies one or more tracking quality metric criteria. The selected angles may correspond to the optimal angles to use for generating tracking images that can be used to track the target during a treatment stage. In one embodiment, at least a first angle in the subset has a separation of at least 15 degrees from a second angle in the subset.

In one embodiment, a processing device determines a set of angles that have a tracking quality metric value that satisfies one or more tracking quality metric criteria. The processing device may be a component of a radiation therapy apparatus (also referred to herein as an image-guided radiation treatment (IGRT) apparatus) that includes a gantry that rotates at a speed of greater than one rotation per minute during a treatment stage. During an alignment phase or a treatment phase of a treatment stage, multiple operations may be performed to track a target. At least a first angle and a second angle may be selected from the set of angles for a first rotation of the gantry. An imaging device mounted to the gantry may then generate a first tracking image of the target from the first angle during the first rotation of the gantry. Subsequently, the imaging device may generate a second tracking image of the target from the second angle during the first rotation of the gantry. The processing device may perform target tracking based on the first tracking image and the second tracking image.

Referring now to the figures, FIG. 1 illustrates a radiation treatment environment 100 within which one or more embodiments as discussed herein may be applied. The radiation treatment environment 100 includes a reference imaging system 102 and an IGRT delivery system 104. Reference imaging system 102 usually comprises a high precision volumetric imaging system such as a computed tomography (CT) system or a nuclear magnetic resonance imaging (MRI) system. In view of cost and workflow considerations in many clinical environments, the reference imaging system 102 is often a general purpose tool used for a variety of different purposes in the clinic or hospital environment, and is not specifically dedicated to the IGRT delivery system 104. Rather, the reference imaging system 102 is often located in its own separate room or vault and is purchased, installed, and/or maintained on a separate and more generalized basis than the IGRT delivery system 104. Accordingly, for the example of FIG. 1, the reference imaging system 102 is illustrated as being distinct from the IGRT delivery system 104. Notably, for other radiation treatment environments that are not outside the scope of the present teachings, the reference imaging system 102 can be considered as an integral component of the IGRT delivery system 104.

A treatment planning system 118 receives the imaging data from the reference imaging system 102 and performs one or more treatment planning operations. Treatment planning system 118 includes a processing device 170 to generate and modify treatment plans and/or simulation plans. Processing device 170 may represent one or more general-purpose processors (e.g., a microprocessor), special purpose processor such as a digital signal processor (DSP) or other type of device such as a controller or field programmable gate array (FPGA). Processing device 170 may be configured to execute instructions for performing simulation generating operations and/or treatment planning operations discussed herein.

Treatment planning system 118 may also include system memory 177 that may include a random access memory (RAM), or other dynamic storage devices, coupled to processing device 170 by a bus, for storing information and instructions to be executed by processing device 170. System memory 177 also may be used for storing temporary variables or other intermediate information during execution of instructions by processing device 170. System memory 177 may also include a read only memory (ROM) and/or other static storage device coupled to the bus for storing static information and instructions for processing device 170.

Treatment planning system 118 may also include A storage device 180, representing one or more storage devices (e.g., a magnetic disk drive, optical disk drive, solid state drive, etc.) coupled to the bus for storing information and instructions. Storage device 180 may be used for storing instructions for performing the treatment planning steps discussed herein, such as treatment planning operations to select a set of imaging angles.

Processing device 170 may also be coupled to a display device, such as a cathode ray tube (CRT) or liquid crystal display (LCD), for displaying information (e.g., a 2D or 3D representation of the VOI) to a user. An input device, such as a keyboard, may be coupled to processing device 170 for communicating information and/or command selections to processing device 170. One or more other user input devices (e.g., a mouse, a trackball or cursor direction keys) may also be used to communicate directional information, to select commands for processing device 170 and to control cursor movements on the display.

Treatment planning system 118 may share its database (e.g., data stored in storage 180) with IGRT delivery system 104, so that it may not be necessary to export from the treatment planning system 118 prior to treatment delivery. Treatment planning system 118 may be linked to IGRT delivery system 104 via a data link, which may be a direct link, a LAN link or a WAN link. It should be noted that when data links are implemented as LAN or WAN connections, any of reference imaging system 102, treatment planning system 118 and/or IGRT delivery system 104 may be in decentralized locations such that the systems may be physically remote from each other. Alternatively, any of reference imaging system 102, treatment planning system 118, and/or IGRT delivery system 104 may be integrated with each other in one or more systems.

In common clinical practice, treatment planning is performed on a pre-acquired treatment planning image 106 generated by the reference imaging system 102. The pre-acquired treatment planning image 106 is often a high resolution three-dimensional CT scan image acquired substantially in advance (e.g., one to two days in advance) of the one or more radiation treatment fractions that the patient will undergo. The pre-acquired treatment planning image 106 may also be a four-dimensional CT scan image. As indicated in FIG. 1 by the illustration of an (i, j, k) coordinate system for the pre-acquired treatment planning image 106, which is in contrast to the (x, y, z) treatment room coordinate system illustrated for the treatment room of the IGRT delivery system 104, there is generally no pre-existing or intrinsic alignment or registration between the treatment planning image 106 coordinate system and the treatment room coordinate system.

During the treatment planning process, a physician establishes a coordinate system (e.g., i, j, k in treatment planning image 106) within the treatment planning image, which may also be referred to herein as the planning image coordinate system or planning image reference frame. A radiation treatment plan is developed in the planning image coordinate system that dictates the various orientations, sizes, durations, etc., of the high-energy treatment radiation beams to be applied by the radiation treatment source 108 during each treatment fraction or stage. Accurate delivery of therapeutic radiation to a target includes aligning the planning image coordinate system with the treatment room coordinate system, as the entire delivery and tracking system (if present) is calibrated to the treatment room coordinate system. It will be appreciated that this alignment does not need to be exact and further appreciated that couch adjustment or beam delivery adjustment can be used to account for offsets in the alignment between the two coordinate systems.

Thus, immediately prior to each treatment fraction (also referred to as a treatment stage), under a precise image guidance of the imaging devices 110, according to one or more of the embodiments described further hereinbelow, the patient is physically positioned such that the planning image coordinate system (defined, for example and not by way of limitation, by a physician while creating a treatment plan on a CT image or planning image) is positioned into an initial alignment with the treatment room coordinate system, hereinafter termed an initial treatment alignment or initial treatment position. This alignment is commonly referred to as patient set up. Depending on the location of the target volume, the target volume can vary in position and orientation and/or can undergo volumetric deformations due to patient movement and/or physiological cycles such as respiration.

As used herein, the term in-treatment alignment variation or in-treatment position variation is used to refer to the variations in position, orientation, and/or volumetric shape by which the current state of the target volume differs from the initial treatment alignment. By virtue of a known relationship between the treatment planning coordinate system and the treatment room coordinate system, the term in-treatment alignment variation can also be used to refer to the variations in position, orientation, or volumetric shape by which the current state of the target volume differs from that in the treatment planning coordinate system. More generally, the term initial treatment alignment or initial treatment position refers herein to the particular physical pose or disposition (including position, orientation and volumetric shape) of the body part of the patient upon patient setup at the outset of the treatment fraction.

IGRT delivery system 104 comprises a radiation treatment (MV) source 108 that selectively applies high-energy x-ray treatment radiation to a target volume of a patient P positioned on a treatment couch TC. In one common scenario, the radiation treatment (MV) source 108 is a linear accelerator (LINAC) producing therapeutic radiation (which can be termed an "MV source"). The radiation treatment source 108 applies the treatment radiation under the control of a system controller 114, and more particularly a treatment radiation control subsystem 128 thereof. System controller 114 may be a computing device that includes a processing device such as discussed above with reference to processing device 170. System controller 114 may also include a system memory and a storage device, similar to system memory 177 and storage device 180. System controller 114 further a detector controller 122, a couch position controller 124, and an imaging device controller 126, each programmed and configured to achieve one or more of the functionalities described further herein. One or more imaging devices 110 selectively emit relatively low-energy (e.g., kV level) x-ray imaging radiation under the control of imaging device controller 126, the imaging radiation being captured by one or more imaging detectors 112.

For one embodiment, the imaging devices 110 include a single x-ray imaging source. In other embodiments, the imaging devices 110 include pair of x-ray imaging sources usable to generate two-dimensional stereotactic x-ray images. The imaging devices 110 may also include a pair of x-ray imaging sources that are in fixed positions and a single x-ray imaging source that is on a rotatable gantry. Preferably, each of the imaging devices 110 are characterized by either (a) a fixed, predetermined, nonmoving geometry relative to the (x, y, z) coordinate system of the treatment room, or (b) a precisely measurable and/or precisely determinable geometry relative to the (x, y, z) coordinate system of the treatment room in the event they are dynamically moveable. The radiation treatment source 108 should also have a precisely measurable and/or precisely determinable geometry relative to the (x, y, z) coordinate system of the treatment room.

An imaging system of the IGRT delivery system 104 comprises one or more independent imaging devices 110 that produce relatively low intensity lower energy imaging radiation (each of which can be termed a "kV source"). In-treatment images can comprise multiple two-dimensional images (typically x-ray images) acquired at multiple different points of view (e.g., e.g., from multiple different angles), and may be compared with two-dimensional DRRs derived from the three-dimensional pre-treatment image information (e.g., from a CT scan or MRI scan). A DRR is a synthetic x-ray image generated by casting hypothetical x-rays through the 3D imaging data, where the direction and orientation of the hypothetical x-rays simulate the geometry of the in-treatment x-ray imaging system. The resulting DRR then has approximately the same scale and point of view as the in-treatment x-ray imaging system, and can be compared with the in-treatment x-ray images to determine the position and orientation of the target, which is then used to guide delivery of radiation to the target.

Target or target volume tracking during treatment may be accomplished by comparing in-treatment tracking images to pre-treatment image information. Pre-treatment image information may comprise, for example, computed tomography (CT) data, cone-beam CT data, magnetic resonance imaging (MRI) data, positron emission tomography (PET) data or 3D rotational angiography (3DRA) data, and any information obtained from these imaging modalities (for example and without limitation digitally reconstructed radiographs or DRRs).

A couch positioner 130 is actuated by the couch position controller 124 to position the treatment couch TC. A non-x-ray based position sensing system 134 may sense position and/or movement of external marker(s) strategically affixed to the patient, and/or sense position and/or movement of the patient skin surface itself, using one or more methods that do not involve ionizing radiation, such as optically based or ultrasonically based methods.

In one embodiment, IGRT delivery system 104 is a gantry based IGRT delivery system. In another embodiment, the IGRT delivery system 104 is a robotic arm based IGRT delivery system. IGRT delivery system 104 further includes an operator workstation 116.

A non x-ray based position sensing system 134 may also be provided. This non x-ray based position sensing system 134 may include, by way of example and without limitation, external markers affixed in some manner to a patient's chest which move in response to respiration (other mechanisms for monitoring respiration may be used), and include a mono or stereoscopic x-ray imaging system, which as described above can precisely determine target location. System 134 correlates motion of the external markers with target motion, as determined from (for example) the mono or stereoscopic tracking images generated by imaging device 110. Non x-ray based position sensing system 134, therefore, permits system controller 114 to monitor external marker motion, use the correlation model to precisely predict where the target will be located in real time (e.g., ~60 Hz), and direct the treatment beam to the target. As treatment of the moving target progresses additional x-ray images may be obtained and used to verify and update the correlation model.

According to one embodiment, system controller 114, including processing device 120, is configured and programmed to receive information from the non-x-ray based position sensing system 134 and/or the imaging detector(s) 112 when treating a relatively stationary target volume (for example and without limitation a brain, spine or prostate tumor), compute an in-treatment alignment variation therefrom, and control the treatment radiation source 108 in a manner that compensates for the in-treatment alignment variation on a continual basis. In the case where the target volume moves due to respiration, the more information-rich data from imaging detectors 112 (e.g., x-ray-based data) is updated at a relatively slow rate compared to the breathing cycle of the patient (for example, once every 15 seconds) to maintain reasonably low x-ray imaging dose levels. The less information-rich data from the non-x-ray based position sensing system 134 can be updated in substantially real-time (for example, 30 times per second). A correlation model between one or more x-ray-sensed internal target volume (with our without fiducials) and one or more non-x-ray-sensed external markers may be used to ascertain the in-treatment alignment variations on a real-time basis. The correlation model may be updated (corrected) at each x-ray imaging interval to maintain accuracy. Advantageously, judicious imaging device 110 angle selection strategies according to one or more of the embodiments described herein can be used to improve target tracking accuracy.

It is to be appreciated that the use of a non-x-ray based position sensing system 134 such as the SYNCHRONY® respiratory tracking system represents an option that, while advantageous in the radiation treatment of certain tumors within the lung or chest area, is not required for radiation treatments in many other body parts, such as the prostate, spine or brain. Whereas x-ray dosage concerns provide limits on the number of kV x-ray images that should be acquired in any particular intrafraction time interval (for example, no more than one kV image every 15 seconds, every 30 seconds, or every 60 seconds), tumors within the chest area, liver or pancreas can move at substantially faster periodic rates due to respiration, therefore giving rise to the usefulness of the non-x-ray based position sensing system 134. However, tumors in other parts of the body, such as the prostate, spine or brain, will generally experience motion on a much slower time scale, wherein the dose-limited kV x-ray imaging rate will be still be sufficiently high to effectively guide the radiation treatment. The prostate, for example, may experience quasi-static movement due to an accumulation of urine in the nearby urinary bladder, an event for which one kV x-ray image every 60 seconds may be sufficient to track resultant movement. Accordingly, for the many other parts of the anatomy for which kV imaging rates are sufficient, the non-x-ray based position sensing system 134 and the associated "real time" tracking (i.e., tracking at a rate faster than the kV imaging rate) may not be used.

It is to be appreciated that the exemplary radiation treatment environment of FIG. 1 is presented by way of example and not by way of limitation. Embodiments are applicable in a variety of other radiation treatment environment configurations, and one or more of the embodiments is applicable to general medical imaging environments outside the particular context of radiation treatment systems. Thus, for example, while one or more of the embodiments is particularly advantageous when applied in the context of a radiation treatment environment in which the reference imaging system 102 is physically separated from, has no common coordinate system with, and/or has no other intrinsic means of volumetric image registration with the IGRT delivery system 104, the scope of the present teachings is not so limited. Rather, embodiments can also be advantageously applied in the context of radiation treatment environments in which the reference imaging system is physically integral with radiation treatment delivery system or has other intrinsic linkages, such as a rail-based patient movement system, with the radiation treatment delivery system.

As used herein, "registration" of images refers to the determination of a mathematical relationship between corresponding anatomical or other (e.g. fiducial) features appearing in those images. Registration can include, but is not limited to, the determination of one or more spatial transformations that, when applied to one or both of the images, would cause an overlay of the corresponding anatomical features. The spatial transformations can include rigid-body transformations and/or deformable transformations and can, if the images are from different coordinate systems or reference frames, account for differences in those coordinate systems or reference frames. For cases in which the images are not acquired using the same imaging system and are not acquired at the same time, the registration process can include, but is not limited to, the determination of a first transformation that accounts for differences between the imaging modalities, imaging geometries, and/or frames of reference of the different imaging systems, together with the determination of a second transformation that accounts for underlying anatomical differences in the body part that may have taken place (e.g., positioning differences, overall movement, relative movement between different structures within the body part, overall deformations, localized deformations within the body part, and so forth) between acquisition times.

In some embodiments at least one imaging device 110 is mounted to a rotatable gantry. The treatment radiation source 108 may or may not be mounted to the rotatable gantry. The at least one imaging device 110 may generate tracking images of a target from multiple different angles. In one embodiment, as discussed in greater detail below, treatment planning system 118 and/or IGRT delivery system 104 determines a set of angles that may be used to generate tracking images by the imaging device 110. As also discussed below, in embodiments IGRT delivery systems may perform target tracking based on tracking images taken at one or more angles from the determined set of angles.

FIGS. 2-6 are flow charts illustrating various methods of selecting angles for use during a treatment stage. The methods of FIGS. 2-6 may be performed prior to treatment and may be referred to as pre-treatment angle selection methods. The methods may be performed by a processing logic that may comprise hardware (e.g., circuitry, dedicated logic, programmable logic, microcode, etc.), software (e.g., instructions run on a processing device to perform hardware simulation), or a combination thereof. The methods of FIGS. 2-6 may be performed by processing logic of a treatment planning system (e.g., treatment planning system 118 of FIG. 1) and/or by processing logic of an IGRT delivery system (e.g., IGRT delivery system 104 of FIG. 1) in embodiments. After the angles are selected, an imaging device that is a component of an IGRT delivery system may use a subset of the selected angles to generate tracking images and track a target during a treatment stage.

Figure 2:
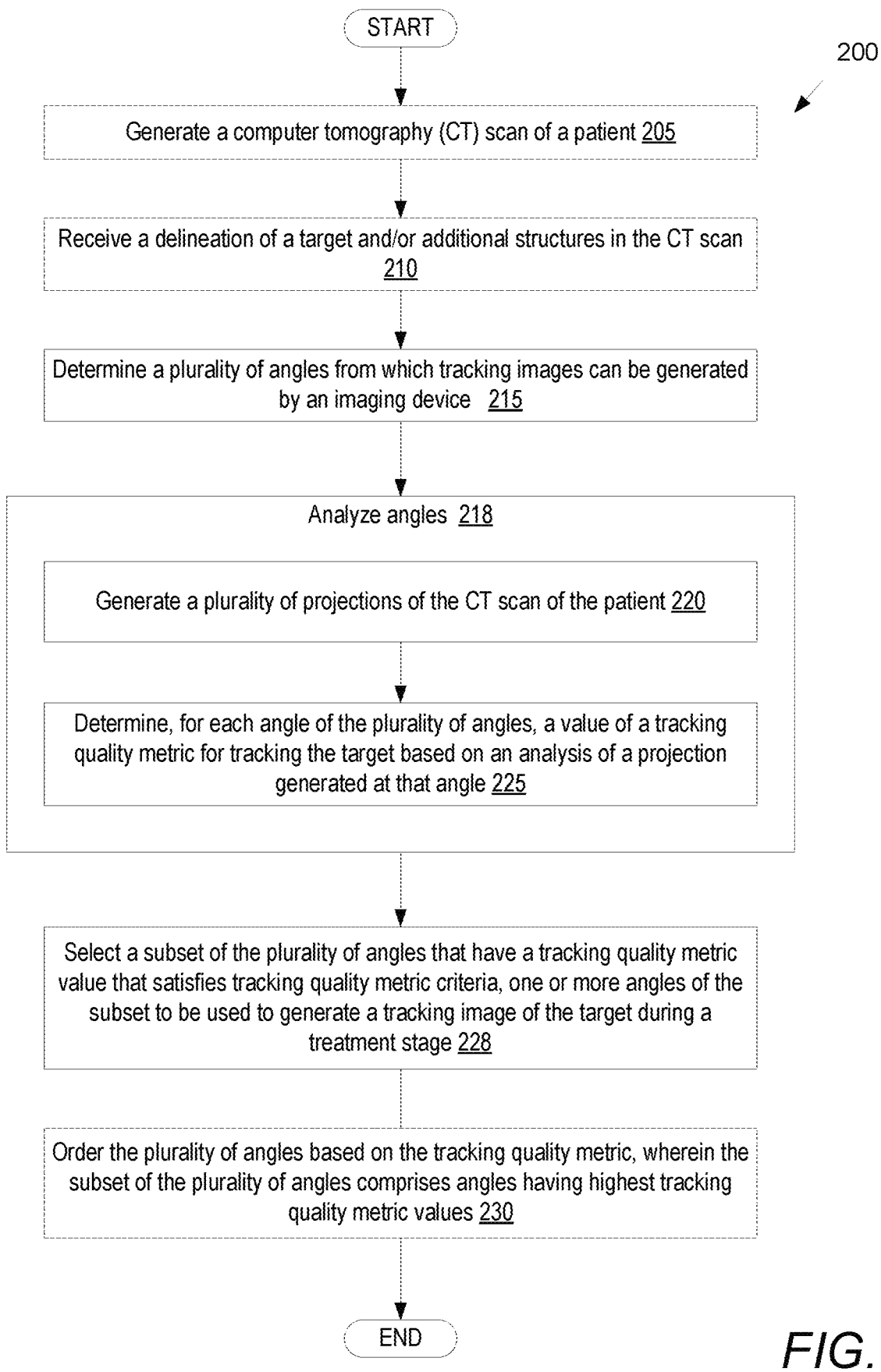
FIG. 2 illustrates a method of selecting a set of angles for use by a rotational imaging device to be used during treatment, in accordance with one embodiment of the present invention.

FIG. 2 illustrates a method 200 of selecting a set of angles for use by a rotational imaging device to be used during treatment, in accordance with one embodiment of the present invention. Method 200 may begin by generating a three-dimensional treatment planning image of a patient at block 205. In one embodiment, as illustrated, the three-dimensional treatment planning image is a computer tomography (CT) scan of the patient. The CT scan may be a three-dimensional (3D) CT scan or a four-dimensional (4D) CT scan. Other three-dimensional treatment planning images or 4D treatment planning images using other image modalities may also be used. Method 200 will be discussed with reference to a CT scan. However, it should be understood that method 200 may be performed using any other three-dimensional or four-dimensional treatment planning images. For example, at block 205 an MRI image may be generated instead of a CT scan image. The MRI image may be a 3D MRI image (also referred to as a 3D MRI scan) or a 4D MRI image (also referred to as a 4D MRI scan).

Once the CT scan is generated, a physician and/or technician may delineate a target within the CT scan at block 210. This may include delineating the target in multiple different slices of the CT scan. After the target has been delineated, the target location and shape is known in 3D space in the CT scan. In addition, additional structures may also be delineated, such as a spine, a heart, a liver, a humerus, a mediastinum, and so on. The additional structures that are delineated may be dense structures in the patient. The operations of blocks 205 and 210 may have already been performed in some embodiments, and may not be a part of method 200. In such embodiments, method 200 may begin by receiving a pre-generated CT scan in which the target and/or additional structures have already been delineated.

At block 215, processing logic determines a plurality of angles from which tracking images can be generated by an imaging device (e.g., by imaging device 110 of FIG. 1). The imaging device may be mounted to a rotatable gantry that may rotate 360 degrees about an axis. Images may be taken from any of the possible angles of the imaging device. In some embodiments, a radiation treatment source is also mounted to the rotatable gantry. Depending on a mode of operation, the rotatable gantry may continuously rotate during a treatment stage, and may generate tracking images from any of the possible angles while rotating. Alternatively, the rotatable gantry may rotate to specific angles and stop at those angles to take tracking images during a treatment stage.

At block 218, processing logic analyzes each of the determined angles. Analysis of the angles may include generating, at block 220, a plurality of projections of the CT scan of the patient. Each of the projections is generated for a different angle at which the imaging device may be positioned. In one embodiment, 360 projections are generated for angles 1 degree through 360 degrees. Thus, the projections may be generated for every 1 degree of angle separation. Alternatively, projections may be generated, for example, at every 5 degrees of angle separation (e.g., at 5 degrees, 10 degrees, 15 degrees, and so on), at every 10 degrees of angle separation, at every 0.5 degree of angle separate, and so on. Multiple different types of projections may be generated, as discussed below with reference to FIGS. 3A-3D. Some examples of projections that may be generated include digitally reconstructed radiographs (DRRs), geometric projections, ray traces of one or more rays, and so on. A DRR is a virtual x-ray image that is generated from a 3D CT image based on simulating the x-ray image formation process by casting rays through the CT image. Any of the projections may be projected onto a virtual detector plane.

Analysis of the angles may further include, at block 225, analyzing the projections generated at the various angles. The analysis that is performed may be dependent on the type of projection that was generated and/or the tracking quality metric criteria to be applied. Some examples of the different analyses that may be performed are described below with reference to FIGS. 3A-6. Based on the analysis, processing logic determines tracking quality metric values for tracking the target at each of the angles for which projections were generated. A tracking quality metric value for an angle represents a confidence that a target tracking algorithm will be able to successfully track the target based on images generated at that angle. In other words, the tracking quality metric value is a value (e.g., a number) that is a proxy for a tracking success probability that enables angles to be ranked and optimal angles to be selected. In one embodiment, a higher tracking quality metric value indicates a higher confidence that the target can be tracked from an angle and a lower tracking quality metric value indicates a lower confidence that the target can be tracked from an angle. Numerous different inputs may be used to compute the tracking quality metric value for an angle. These inputs may be used individually or in combination to compute the tracking quality metric value. Where multiple inputs are used, the inputs may or may not be weighted. Examples of different tracking quality metric values (and inputs for tracking quality metric values) are discussed with reference to FIGS. 3A-6 below.

At block 228, processing logic selects a subset of the angles for which projections were generated. Angles may be selected for inclusion in the subset based on the tracking quality metric values associated with those angles. The angles that are selected for inclusion in the subset have a tracking quality metric value that satisfies a tracking quality metric criterion (or multiple tracking quality metric criteria). In one embodiment, the tracking quality metric criteria include a tracking quality metric threshold. Those angles associated with tracking quality metric values that meet or exceed the tracking quality metric threshold may be included in the subset, while those angles associated with tracking quality metric values below the threshold may not be included in the subset. The tracking quality metric threshold may be a fixed threshold or a variable threshold. For a variable threshold, the threshold may be determined based on the computed tracking quality metric values for a particular patient. For example, if the highest tracking quality metric value was 0.6, then the threshold may be 0.5. For a fixed threshold, the threshold may be determined without consideration of the computed tracking quality metric values for a particular patient. In some instances that may lead to there being no angles that satisfy the tracking quality metric criteria.

At block 230, processing logic may order the angles based on their associated tracking quality metric values. The subset of angles to be used for tracking purposes may be those angles having highest tracking quality metric values. Accordingly, optimal angles may be determined for the purpose of generating images to track a target during a treatment stage of a patient.

In some instances, processing logic may determine that there is an insufficient number of angles in the subset that have the tracking quality metric value that satisfies the one or more tracking quality metric criteria. One possible cause for an insufficient number of available angles is a large distance between the target and a treatment isocenter. Accordingly, if there is an insufficient number of angles in the subset, processing logic may output a suggestion that the patient be repositioned to cause the target to be closer to the treatment isocenter. For example, processing logic may recommend that the patient be repositioned 4 cm to the left. Patient repositioning may be performed by physically repositioning the patient on a treatment couch or by automatically moving the treatment couch vertically and/or laterally. After the repositioning, method 200 may be repeated to determine a new subset of the plurality of angles.

FIGS. 3A-3D illustrate various methods for computing tracking quality metric values for possible angles of an imaging device. Any one of these methods may be performed at block 218 of method 200 to determine quality metric values for the different angles. Additionally or alternatively, two of more of these methods may be combined to determine multiple quality metric values for each angle or to determine a single combined quality metric value based on the different methods. If multiple methods are used, then the quality metric values output by each of these methods may be weighted equally or unequally to compute a final combined quality metric value.

Figure 3A:
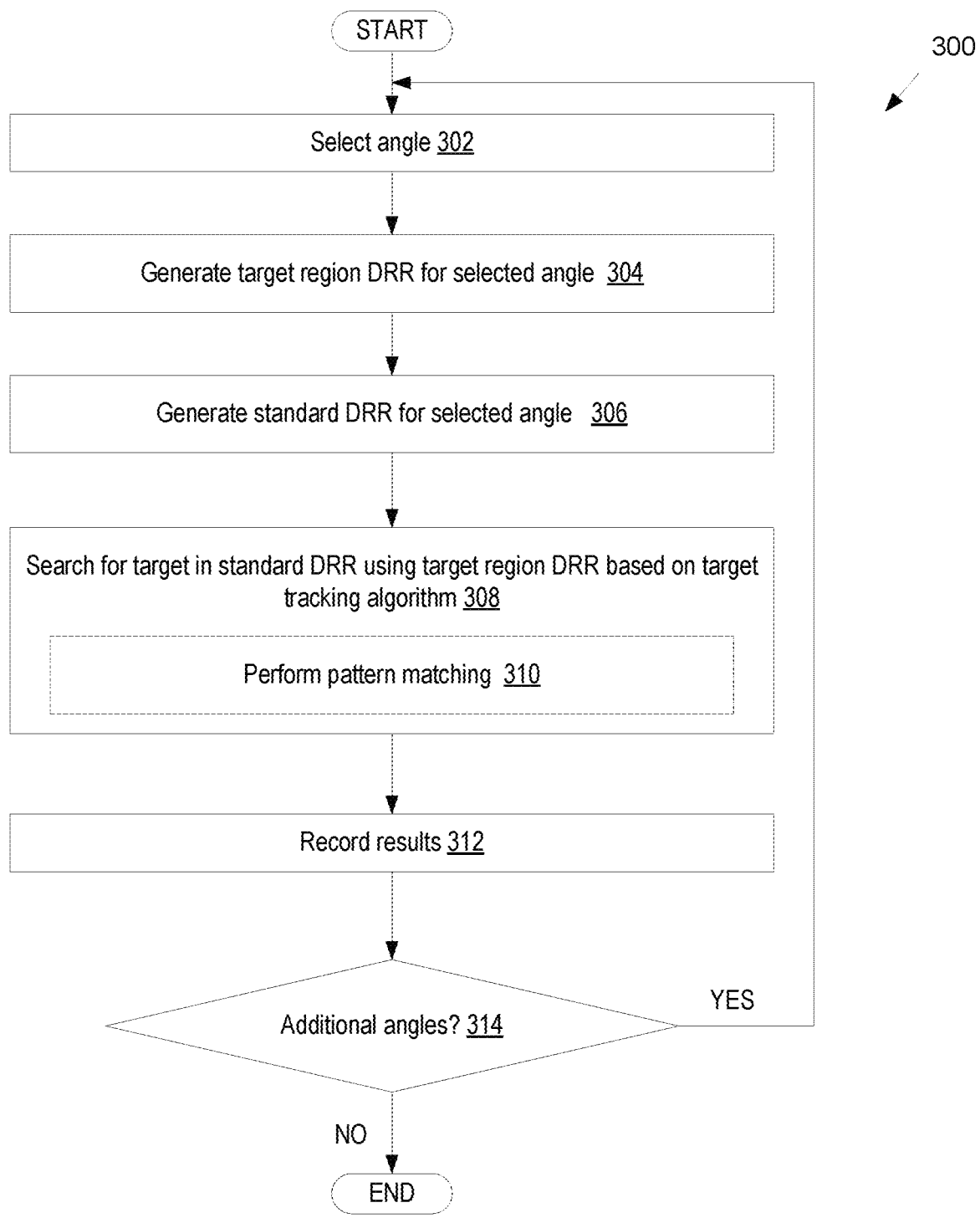
FIG. 3A illustrates a first method of determining tracking quality metric values for angles of a rotational imaging device, in accordance with one embodiment of the present invention.

FIG. 3A illustrates a first method 300 of determining tracking quality metric values for angles of a rotational imaging device, in accordance with one embodiment of the present invention. At block 302 of method 300 processing logic selects an angle. The selected angle corresponds to an angle of an imaging device that can be used to generate tracking images. At block 304, processing logic generates a target region DRR for the selected angle. A target region DRR is a DRR that is generated by casting or tracing rays through just the target in a CT scan or other treatment planning image (e.g., an MRI image). DRR pixel values may be computed by summing CT values along each ray. At block 306, a standard DRR is generated for the selected angle. T The standard DRR differs from the target region DRR in that the rays are traced through all regions of the CT scan (or other treatment planning image) to generate the standard DRR. For both the standard DRR and the target region DRR the rays may be traced onto a virtual detector plane. Each pixel of the virtual detector plane may correspond to a ray traced through the CT scan data (or other treatment planning image data). The pixel value for a pixel may be based on an aggregation of the CT values of the associated ray.

At block 308, processing logic uses a target tracking algorithm to search for the target in the standard DRR using the target region DRR. The target tracking algorithm may be the same target tracking algorithm that will be used to track the target during a treatment stage for treatment of the patient. However, during treatment the target tracking algorithm may find the target in tracking images such as x-ray images.

In one embodiment, the target tracking algorithm performs pattern matching based on similarity values between the target region DRR and the standard DRR, as described in the example below and indicated in block 310. In such an example, the target tracking algorithm determines characteristics or patterns such as a shape of the target from the target region DRR. The target tracking algorithm computes similarity values between a first pattern of the target from the target region DRR and patterns for each of several candidate locations for the target in the standard DRR. The maximum of similarity values between the first pattern from the target region DRR and the additional patterns from the standard DRR indicates a location of the target in the standard DRR. The tracking quality metric value may be proportional to the degree of similarity between the first pattern and the closest pattern from the standard DRR in some embodiments.

A similarity value for a candidate location may be based on a combination of similarity values for the target region DRR at the candidate location. "Similarity values" or "similarity measures" are numbers that reflect the degree to which two images are similar to each other. For example, a cross-correlation or combination of several cross-correlations between two images can be used to compute a similarity value. One embodiment for locating a target proceeds by assembling a similarity map over a tracking region for the target region DRR. The similarity map contains a similarity value for the DRR at each of the candidate locations considered in the image. Similarity values as described above may be computed using, but not limited to, cross-correlation, entropy, mutual information, gradient correlation, pattern intensity, gradient difference, or image intensity gradients methods. The computed values may be normalized so that the resulting similarity value is a number ranging between 0 and 1 or −1 and 1. The highest similarity value may be used to generate a tracking quality metric value for the selected angle.

The target may not be located in the standard DRR based on the target region DRR in some instances. For example, the target may not be located if the target is occluded by a bone structure or other dense structure such as the heart or diaphragm. Failure to locate the target may result in a tracking quality metric value that fails to satisfy a tracking quality metric criterion.

In some embodiments, the tracking quality metric value is a confidence value. The tracking quality metric value may be based on the highest similarity value for a candidate location. The tracking quality metric value may also be based on a difference between the highest similarity value for a candidate location and other similarity values for other candidate locations. If a difference between the highest similarity value and other similarity values is below a difference threshold, this indicates that from the selected angle there are other structures in the patient that resemble the target. Such similar structures may confuse the tracking algorithm during treatment and so cause the confidence value to be reduced. Additionally, the actual location of the target in the standard DRR is known. If the location determined by the target tracking algorithm differs from the known location, then the tracking quality metric value may also be reduced.

At block 312, processing logic records the results of the target tracking algorithm. This may be a single tracking quality metric value such as a confidence value. The results of the target tracking algorithm may alternatively include multiple values, such as a binary success/fail value and a confidence value.

At block 314, processing logic determines if there are any additional angles for which tracking quality metric values still need to be determined. If so, the method returns to block 302 and a new angle is selected. Otherwise the method ends.

Figure 3B:
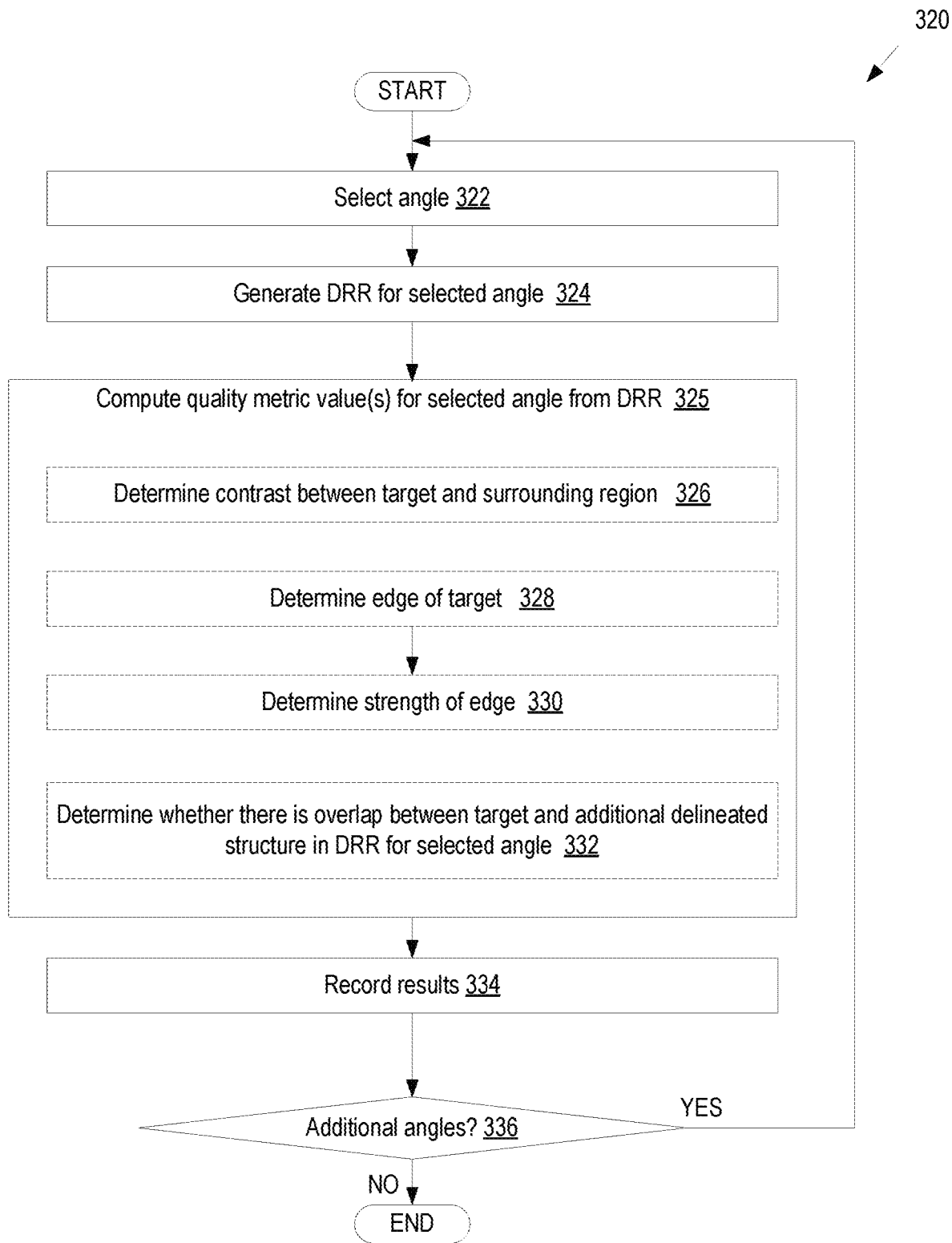
FIG. 3B illustrates a second method of determining tracking quality metric values for angles of a rotational imaging device, in accordance with one embodiment of the present invention.

FIG. 3B illustrates a second method 320 of determining tracking quality metric values for angles of a rotational imaging device, in accordance with one embodiment of the present invention. At block 322 of method 320 processing logic selects an angle. The selected angle corresponds to an angle of an imaging device that can be used to generate tracking images. At block 324, processing logic generates a DRR (e.g., a standard DRR) for the selected angle. At block 325, processing logic computes one or more quality metric values for the selected angle based on the DRR. Multiple different techniques may be used to compute the quality metric values, some of which are described herein. However, this disclosure is not limited only to those techniques described herein for computing the tracking quality metric values. If multiple quality metric values are determined, these values may be combined into a combined quality metric value. The combined quality metric value may be based on a weighted or non-weighted combination of the different quality metric values.

In one embodiment, at block 326 processing logic determines a contrast between the target and a region surrounding the target. The location of the target is known since the target is delineated in the CT scan (or other treatment planning image) used to generate the DRR. The contrast may be a difference in intensities between the target and the background (surrounding region). Accordingly, a contrast between a first region inside of the target and a second region outside of the target may be computed without a need to first locate the target.

There are multiple different contrast values that may be used alone or in combination to compute the tracking quality metric value (or an input for a tracking quality metric value). One contrast value that may be determined is the luminance contrast, which is the difference in intensities between the target and its background (the surrounding region) divided by an intensity of the background. Another contrast value that may be computed is a contrast to noise ratio (CNR). CNR is computed by dividing the luminance contrast by a standard deviation of overall image noise. Noisy images generally require a larger contrast to offer similar visibility of the target. Other types of contrast that may be computed include Weber contrast, Michelson contrast and root mean square (RMS) contrast.

Higher contrast values indicate an increased probability of finding the target during treatment. Accordingly, higher contrast values are preferable. In one embodiment, tracking quality metric criteria include a minimum acceptable contrast and/or a minimum acceptable contrast to noise ratio. The minimum acceptable contrast may be determined based on a combination (e.g., an average) of the contrasts computed for DRRs at multiple different angles. In one embodiment, an angle having a contrast value that is below the minimum acceptable contrast (and/or below the minimum acceptable contrast to noise ratio) fails to satisfy the one or more tracking quality metric criteria.

In one embodiment, at block 328 processing logic determines an edge of the target. The edge of the target may be determined easily because the location of the target is delineated in the CT scan (or other treatment planning image) and so is known. At block 330, processing logic determines an edge strength for the edge of the target. The edge strength may be determined by computing changes in image brightness and/or other image properties at the edge. In one embodiment, a first order derivative of the change in image brightness at the edge is computed. Other mathematical techniques may also be used to compute the edge strength. A higher edge strength indicates a higher likelihood of finding the target during a treatment stage. In one embodiment, tracking quality metric criteria include a minimum acceptable edge strength. In one embodiment, an angle having an edge strength value that is below the minimum acceptable edge strength fails to satisfy the tracking quality metric criteria.

As mentioned previously, the CT scan (or other treatment planning image) from which the DRR is generated at block 324 includes a delineated target and may also include one or more additional delineated structures, such as a spine, heart, diaphragm, and so on. In one embodiment, at block 332 processing logic determines whether there is overlap between the target and an additional delineated structure in the DRR. Overlap between delineated structures may indicate that the target or a portion of the target may not be visible in tracking images taken from the angle, and may cause a target tracking algorithm used during treatment to fail to find the target. In one embodiment, tracking quality metric criteria include a maximum acceptable overlap between the target and additional delineated structures. In one embodiment, tracking quality metric criteria include a minimum acceptable distance between the target and additional delineated structures. In one embodiment, an overlap between the delineated target and an additional delineated structure causes the tracking quality metric value for the angle to fail to satisfy the tracking quality metric criteria.

At block 334, processing logic records the results of the one or more quality metric values. Each of these tracking quality metric values may be inputs for a combined tracking quality metric value. At block 336, processing logic determines if there are any additional angles for which tracking quality metric values still have not been determined. If so, the method returns to block 322 and a new angle is selected. Otherwise the method ends.

Figure 3C:
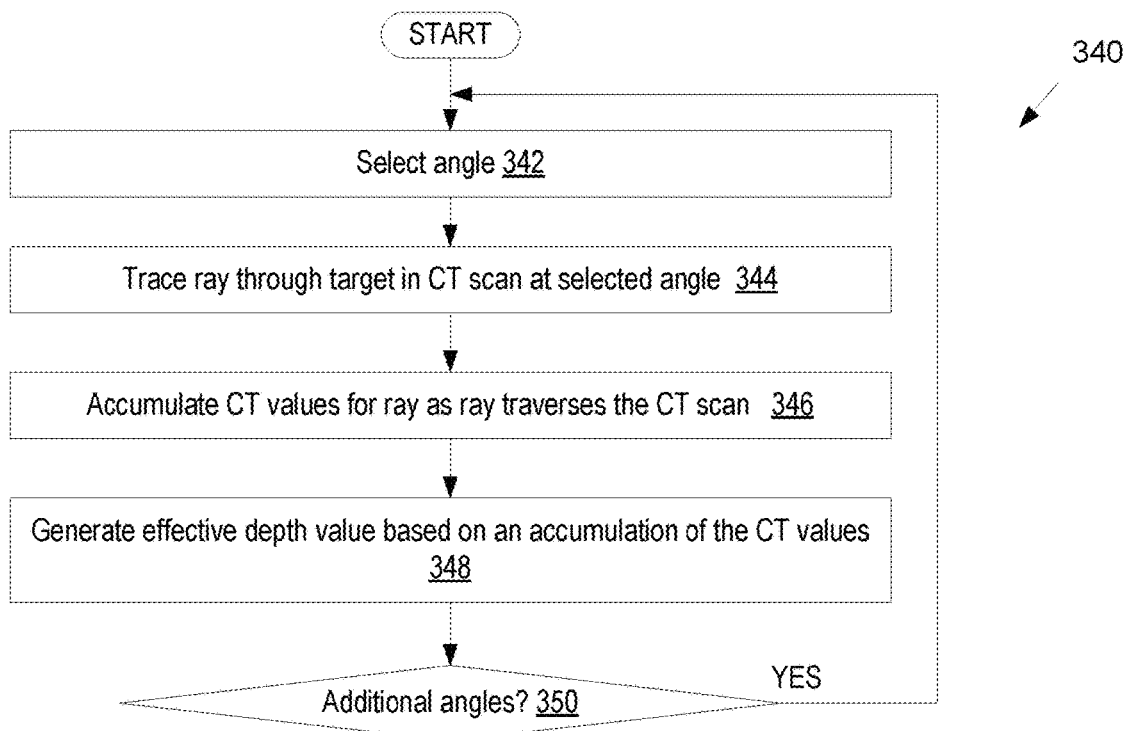
FIG. 3C illustrates a third method of determining tracking quality metric values for angles of a rotational imaging device, in accordance with one embodiment of the present invention.

FIG. 3C illustrates a third method 340 of determining tracking quality metric values for angles of a rotational imaging device, in accordance with one embodiment of the present invention. At block 342 of method 340 processing logic selects an angle. The selected angle corresponds to an angle of an imaging device that can be used to generate tracking images. At block 344, processing logic traces a ray through the target in the CT scan or other treatment planning image at the selected angle. In one embodiment, the ray goes through a centroid of the target. At block 346, processing logic accumulates CT values for the ray as the ray traverses the CT scan.

At block 348, processing logic generates an effective depth value based on an accumulation of the CT values or values of another 3D or 4D treatment planning image. The effective depth value represents a total accumulated density of material traversed by the ray. Higher effective depth values indicate that the ray passed through dense material, whereas lower effective depth values indicate that the ray passed through less dense material. Accordingly, lower effective depth values are preferred in embodiments. The effective depth value for the ray may be a tracking quality metric value for the angle. Alternatively, the effective depth value for the ray may be one input for a tracking quality metric value. In one embodiment, the tracking quality metric criteria include a maximum acceptable effective depth value. In one embodiment, an effective depth value higher than the maximum acceptable effective depth value causes the tracking quality metric value to fail to satisfy the one or more tracking quality metric criteria.

In some embodiments multiple rays are traced through the target at the selected angle, and effective depth values may be determined for each ray. For example, ray tracing may be performed for anywhere from two rays that pass through the target to all rays that pass through the target. The effective depth values may then be mathematically combined to determine a combined effective depth value. In one embodiment, the effective depth values of the multiple rays are averaged to compute an average effective depth value. In one embodiment, a median effective depth value is computed. The combined effective depth value, average effective depth value and/or median effective depth value may be used as the tracking quality metric value or as an input to the tracking quality metric value. The effective depth value (or values) and/or the tracking quality metric value may then be recorded for the angle.

At block 350, processing logic determines if there are any additional angles for which tracking quality metric values still need to be determined. If so, the method returns to block 342 and a new angle is selected. Otherwise the method ends.

Figure 3D:
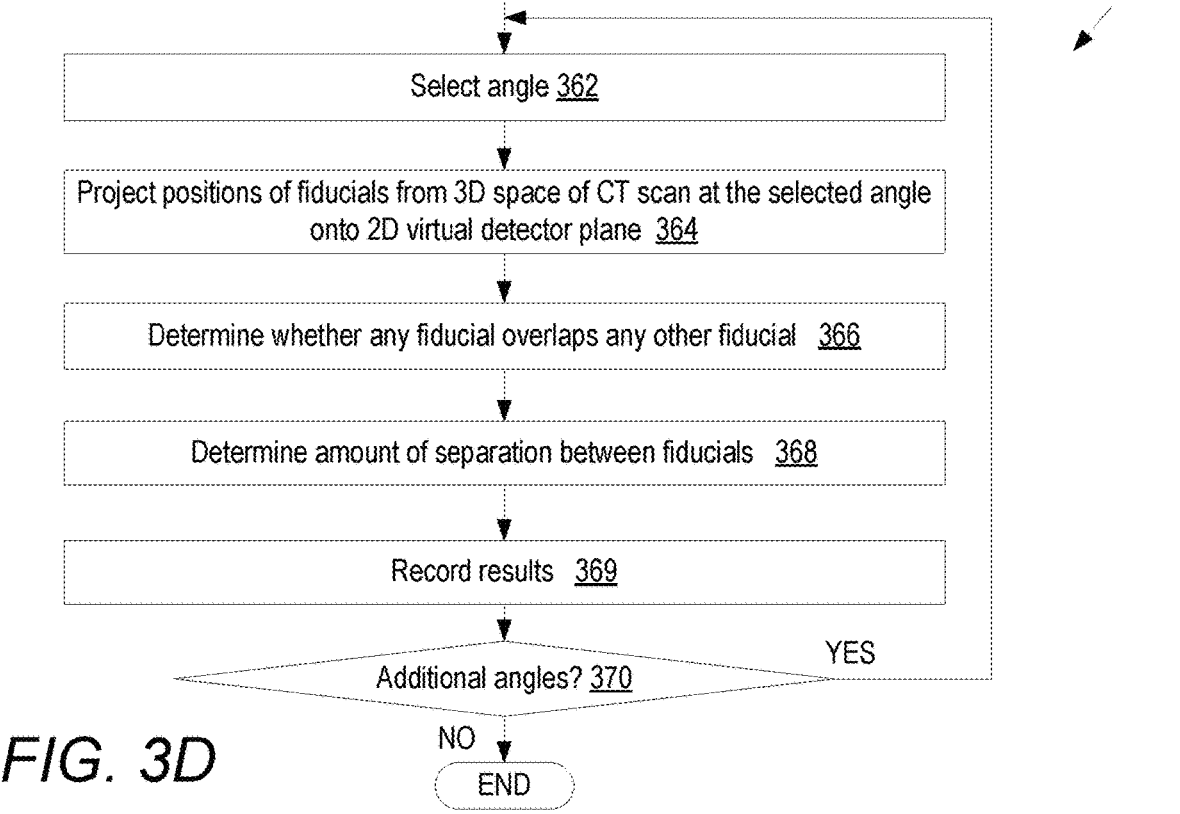
FIG. 3D illustrates a fourth method of determining tracking quality metric values for angles of a rotational imaging device, in accordance with one embodiment of the present invention.

FIG. 3D illustrates a fourth method 360 of determining tracking quality metric values for angles of a rotational imaging device, in accordance with one embodiment of the present invention. Method 360 may be used to determine the tracking quality metric values of tracking a target based on tracking fiducials that are implanted in the target. The target may have multiple fiducials that have been implanted in the target. Tracking of the target in three-dimensional space may be optimal at angles where each of the fiducials is separately viewable in images taken at those angles.

At block 362 of method 360 processing logic selects an angle. The selected angle corresponds to an angle of an imaging device that can be used to generate tracking images. At block 364, processing logic projects positions of the fiducials from a 3D space of the CT scan (or other treatment planning image) at the selected angle onto a 2D virtual detector plane. The projection may be a geometric projection of the fiducials.

At block 366, processing logic determines whether any of the fiducials overlaps with any other fiducial in the target. In one embodiment, a fiducial overlap tracking quality metric criterion is a binary criterion based on whether or not there is overlap between any two fiducials. If there is overlap between fiducials, the fiducial overlap tracking quality metric criterion may not be satisfied for an angle. In one embodiment, a tracking quality metric criterion may be a numeric value based on an allowed amount of overlap between fiducials. Greater overlap between fiducials may result in poorer tracking results, and thus may result in a lower tracking quality metric value.

At block 368, processing logic determines an amount of separation between the fiducials. An amount of separation may be determined between each of the fiducials. For example, if there are three fiducials, then a separation value may be determined between the first and second fiducials, between the second and third fiducials, and between the first and third fiducials. Alternatively, separation values may be computed between closest fiducials in the geometric projection. A higher amount of separation between fiducials may result in better tracking results, and so may be preferred in embodiments. The minimum separation between fiducials for an angle may be used as a tracking quality metric value for that angle. Alternatively, a tracking quality metric value may be computed at least in part based on the minimum separation between fiducials, the average separation, the amount of overlap, and so on.

At block 369, processing logic records the results of the one or more quality metric values. At block 370, processing logic determines if there are any additional angles for which tracking quality metric values are still to be determined. If so, the method returns to block 364 and a new angle is selected. Otherwise the method ends.

Figure 4:
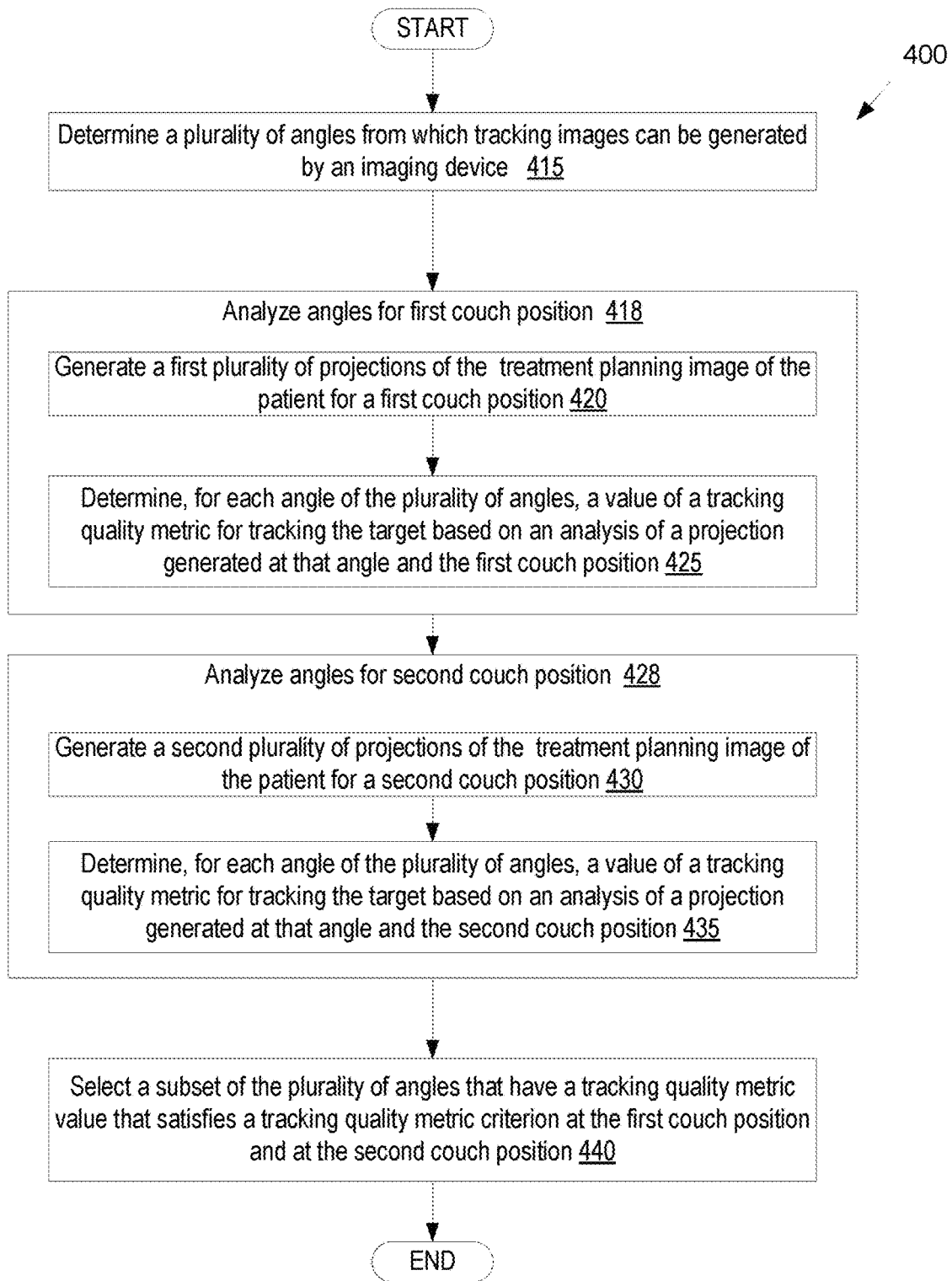
FIG. 4 illustrates a method of selecting a set of angles for use by a rotational imaging device to be used during treatment, in accordance with one embodiment of the present invention.

FIG. 4 illustrates a method 400 of selecting a set of angles for use by a rotational imaging device to be used during treatment, in accordance with one embodiment of the present invention. In certain embodiments method 400 is substantially similar to method 200. Specifically, embodiments of method 400 correspond to performing the operations of method 200 for multiple different couch positions of a movable treatment couch and selecting a subset of angles based on combined results of the tracking quality metric values for the angles at the multiple couch positions.

At block 415, processing logic determines a plurality of angles from which tracking images can be generated by an imaging device (e.g., by imaging device 110 of FIG. 1). The imaging device may be mounted to a rotatable gantry that may rotate 360 degrees about an axis. Images may be taken from any of the possible angles of the imaging device.

At block 418, processing logic analyses the plurality of angles for a first couch position of the treatment couch. At block 420, analysis of the angles includes generating a first plurality of projections of the treatment planning image of the patient for the first couch position. Each of the projections is generated for a different angle at which the imaging device may be positioned. In one embodiment, 360 projections are generated for angles 1 degree through 360 degrees. Thus, the projections may be generated for every 1 degree angle separation. Alternatively, projections may be generated, for example, at every 5 degree angle separation (e.g., at 5 degrees, 10 degrees, 15 degrees, and so on), at every 10 degree angle separation, at every 0.5 degree angle separate, and so on. Multiple different types of projections may be generated, as discussed above with reference to FIGS. 3A-3D. Some examples of projections that may be generated include digitally reconstructed radiographs (DRRs), geometric projections, ray traces of one or more rays, and so on.

Analysis of the angles may further include, at block 425, analyzing the projections generated at the various angles for the first couch position. The analysis that is performed may be dependent on the type of projection that was generated. Examples of the different analyses that may be performed are described above with reference to FIGS. 3A-3D. Based on the analysis, processing logic determines tracking quality metric values for tracking the target for the first couch position and at each of the angles for which projections were generated.

At block 428, processing logic analyses the plurality of angles for a second couch position of the treatment couch. In one embodiment, the first couch position and the second couch position represent two opposite extremes of couch positions that may be used during a treatment stage for the patient.

At block 430, analysis of the angles includes generating a second plurality of projections of the treatment planning image of the patient for the second couch position. Analysis of the angles may further include, at block 435, analyzing the projections generated at the various angles for the second couch position. The analysis that is performed may be dependent on the type of projection that was generated. Examples of the different analyses that may be performed are described above with reference to FIGS. 3A-3D. Based on the analysis, processing logic determines tracking quality metric values for tracking the target for the second couch position and at each of the angles for which projections were generated.

In some embodiments, additional analyses of the plurality of angles may also be performed for additional couch positions. For each such couch position different tracking quality metric values may be determined at each of the plurality of angles.

At block 440, processing logic selects a subset of the angles for which projections were generated. Angles may be selected for inclusion in the subset based on the quality metric values associated with those angles at the multiple different couch positions. The angles that are selected for inclusion in the subset have a tracking quality metric value that satisfies a tracking quality metric criterion (or multiple tracking quality metric criteria) at each of the different couch positions that are considered. In one embodiment, the tracking quality metric criteria include a tracking quality metric threshold. Those angles associated with tracking quality metric values that meet or exceed the tracking quality metric threshold may be included in the subset, while those angles associated with tracking quality metric values below the threshold may not be included in the subset. The tracking quality metric threshold may be a fixed threshold or a variable threshold.

Processing logic may then order the angles based on their associated tracking quality metric values. The subset of angles to be used for tracking purposes may be those angles having highest tracking quality metric values at multiple different couch positions. Accordingly, optimal angles may be determined for the purpose of generating images to track a target during a treatment stage of a patient at a range of possible couch positions that might be used during the treatment stage.

Figure 5:
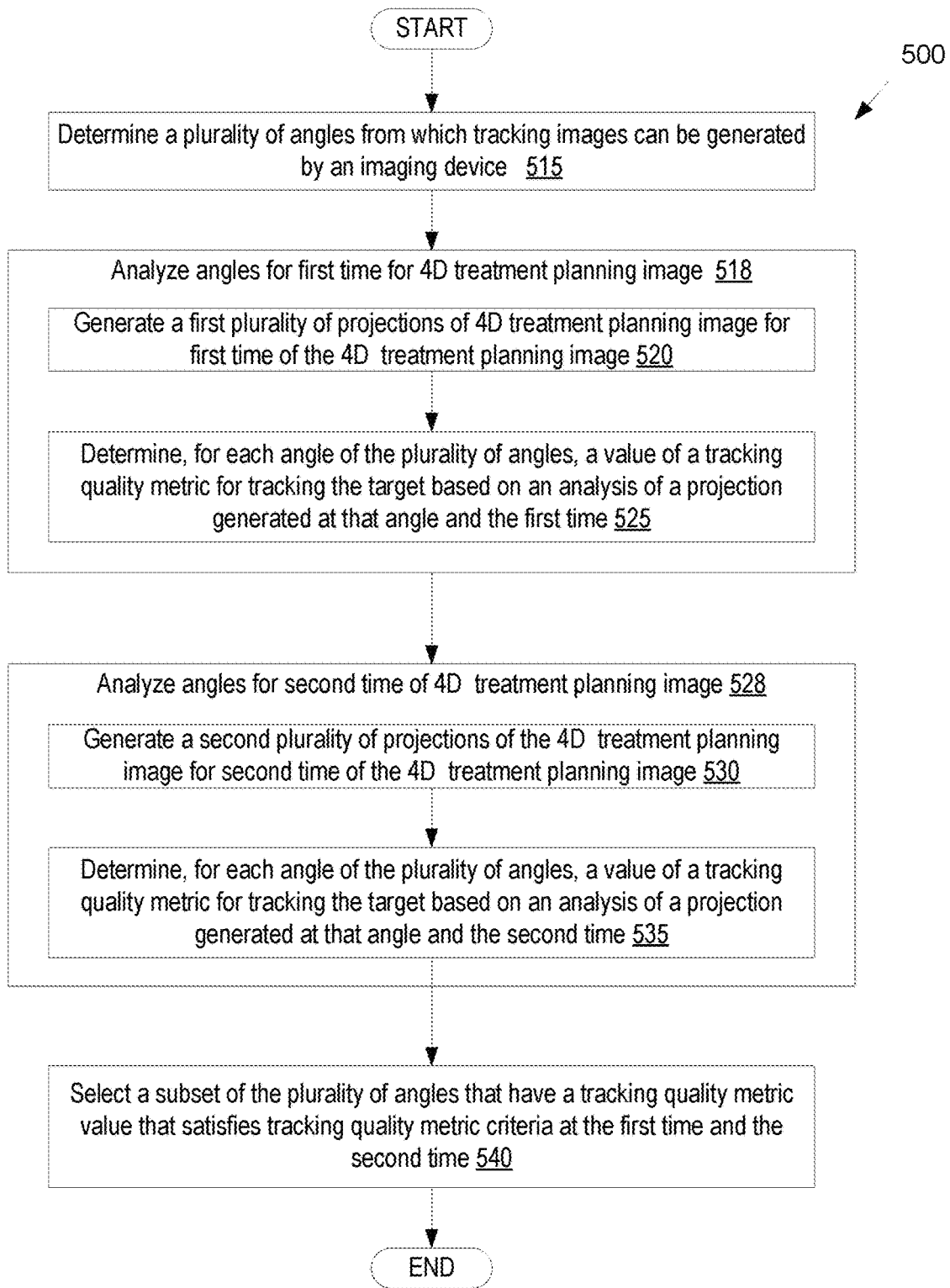
FIG. 5 illustrates a method of selecting a set of angles for use by a rotational imaging device to be used during treatment, in accordance with one embodiment of the present invention.

FIG. 5 illustrates a method 500 of selecting a set of angles for use by a rotational imaging device to be used during treatment, in accordance with one embodiment of the present invention. In certain embodiments method 500 is substantially similar to method 200. Specifically, embodiments of method 500 correspond to performing the operations of method 200 for multiple different times of a 4D CT scan (or other 4D treatment planning image) and selecting a subset of angles based on combined results of the tracking quality metric values for the angles at the multiple different time slices.

At block 515, processing logic determines a plurality of angles from which tracking images can be generated by an imaging device (e.g., by imaging device 110 of FIG. 1). The imaging device may be mounted to a rotatable gantry that may rotate 360 degrees about an axis. Images may be taken from any of the possible angles of the imaging device.

At block 518, processing logic analyses the plurality of angles for a first time of the 4D CT scan (or other 4D treatment planning image). At block 420, analysis of the angles includes generating a first plurality of projections of the CT scan (or other 3D treatment planning image) of the patient for the first time. Each of the projections is generated for a different angle at which the imaging device may be positioned. In one embodiment, 360 projections are generated for angles 1 degree through 360 degrees. Thus, the projections may be generated for every 1 degree angle separation. Alternatively, projections may be generated, for example, at every 5 degree angle separation (e.g., at 5 degrees, 10 degrees, 15 degrees, and so on), at every 10 degree angle separation, at every 0.5 degree angle separate, and so on. Multiple different types of projections may be generated, as discussed above with reference to FIGS. 3A-3D. Some examples of projections that may be generated include digitally reconstructed radiographs (DRRs), geometric projections, ray traces of one or more rays, and so on. A DRR is a virtual x-ray image that is generated from a 3D CT image (or other 3D treatment planning image) based on simulating the x-ray image formation process by casting rays through the CT image (or other 3D treatment planning image). Any of the projections may be projected onto a virtual detector plane.

Analysis of the angles may further include, at block 525, analyzing the projections generated at the various angles for the first time. The analysis that is performed may be dependent on the type of projection that was generated. Examples of the different analyses that may be performed are described above with reference to FIGS. 3A-3D. Based on the analysis, processing logic determines tracking quality metric values for tracking the target for the first time and at each of the angles for which projections were generated.

At block 528, processing logic analyzes the plurality of angles for a second time of the 4D CT scan (or other 4D treatment planning image). In one embodiment, the first time and the second time represent two opposite extremes of position and/or rotation that the target may achieve during a treatment stage for the patient. The target may undergo motion during the treatment stage. The 4D CT scan may capture motion of the target over a time period, and that captured motion may correspond to a motion that the target is likely to also undergo during the treatment stage. Accordingly, it can be beneficial to identify and select angles that will be optimal throughout the motion of the target. Some types of motion that a target may undergo are cyclical motions. For example, targets that are located in the lung region of a patient may move, change shape and/or rotate with inhalation and exhalation of the patient.

At block 530, analysis of the angles includes generating a second plurality of projections of the CT scan (or other treatment planning image) of the patient for the second time of the 4D CT scan (or other 4D treatment planning image). Analysis of the angles may further include, at block 535, analyzing the projections generated at the various angles for the second time of the 4D CT scan (or other 4D treatment planning image). The analysis that is performed may be dependent on the type of projection that was generated. Examples of the different analyses that may be performed are described above with reference to FIGS. 3A-3D. Based on the analysis, processing logic determines tracking quality metric values for tracking the target for the second time and at each of the angles for which projections were generated.

In some embodiments, additional analyses of the plurality of angles may also be performed for additional times of the 4D CT scan or other 4D treatment planning image. For each such time slice different tracking quality metric values may be determined at each of the plurality of angles.

At block 540, processing logic selects a subset of the angles for which projections were generated. Angles may be selected for inclusion in the subset based on the quality metric values associated with those angles at the multiple different times of the 4D CT scan (or other 4D treatment planning image). The angles that are selected for inclusion in the subset have a tracking quality metric value that satisfies a tracking quality metric criterion (or multiple tracking quality metric criteria) at each of the times that are considered. In one embodiment, the tracking quality metric criteria include a tracking quality metric threshold. Those angles associated with tracking quality metric values that meet or exceed the tracking quality metric threshold may be included in the subset, while those angles associated with tracking quality metric values below the threshold may not be included in the subset. The tracking quality metric threshold may be a fixed threshold or a variable threshold.

Processing logic may then order the angles based on their associated tracking quality metric values. The subset of angles to be used for tracking purposes may be those angles having highest tracking quality metric values at multiple times of the 4D CT scan (or other 4D treatment planning image). Accordingly, optimal angles may be determined for the purpose of generating images to track a target at different stages of a cyclic motion that the target may undergo during a treatment stage.

Figure 6A:
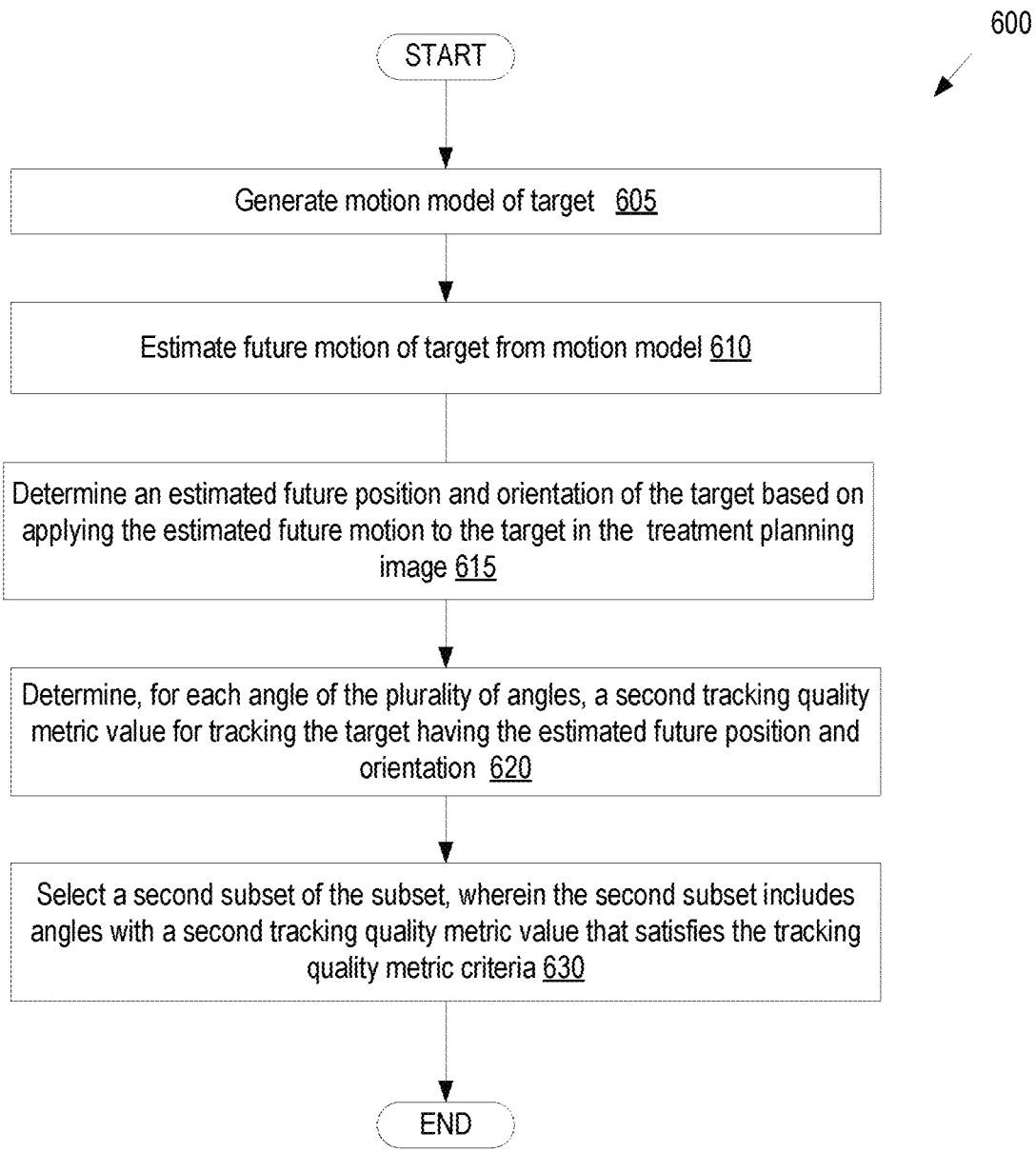
FIG. 6A illustrates a method of selecting a set of angles for use by a rotational imaging device to be used during treatment of a moving target, in accordance with one embodiment of the present invention.

FIG. 6A illustrates a method 600 of selecting a set of angles for use by a rotational imaging device to be used during treatment of a moving target, in accordance with one embodiment of the present invention. In one embodiment, method 600 is performed after block 228 of method 200.

At block 605 of method 600, processing logic generates a motion model of the target. The motion model may be for a cyclic motion (e.g., a motion that occurs with breathing) or for a quasi-static motion. A quasi-static motion is a motion that occurs slowly in a predictable episodic manner. One example of a target that may undergo a quasi-static motion is a prostate. The motion model may be generated based on statistical information about how targets of a particular type generally move. For example, a statistical motion model may be generated for prostate motion based on statistical information about how prostates of many patients have been detected to move. The motion model may alternatively or additionally be based on additional information, such as on a 4D CT scan or 4D magnetic resonance imaging (MRI) image of the patient showing motion of the target.

At block 610, processing logic estimates a future motion of the target from the motion model. At block 615, processing logic determines an estimated future position and orientation (and possibly size and/or shape) of the target based on applying the estimated future motion to the target in the CT scan or other treatment planning image. At block 620, processing logic determines, for each angle of the plurality of angles, a second tracking quality metric value for tracking the target having the estimated future position and orientation. At block 630, processing logic determines a second subset of the subset of angles having tracking quality metric values that satisfy the one or more tracking quality criteria. The second subset may be a further subset that may include less than all of the angles in the subset. The second subset includes angles with a second tracking quality metric value that also satisfies the tracking quality metric criteria.

Figure 6B:
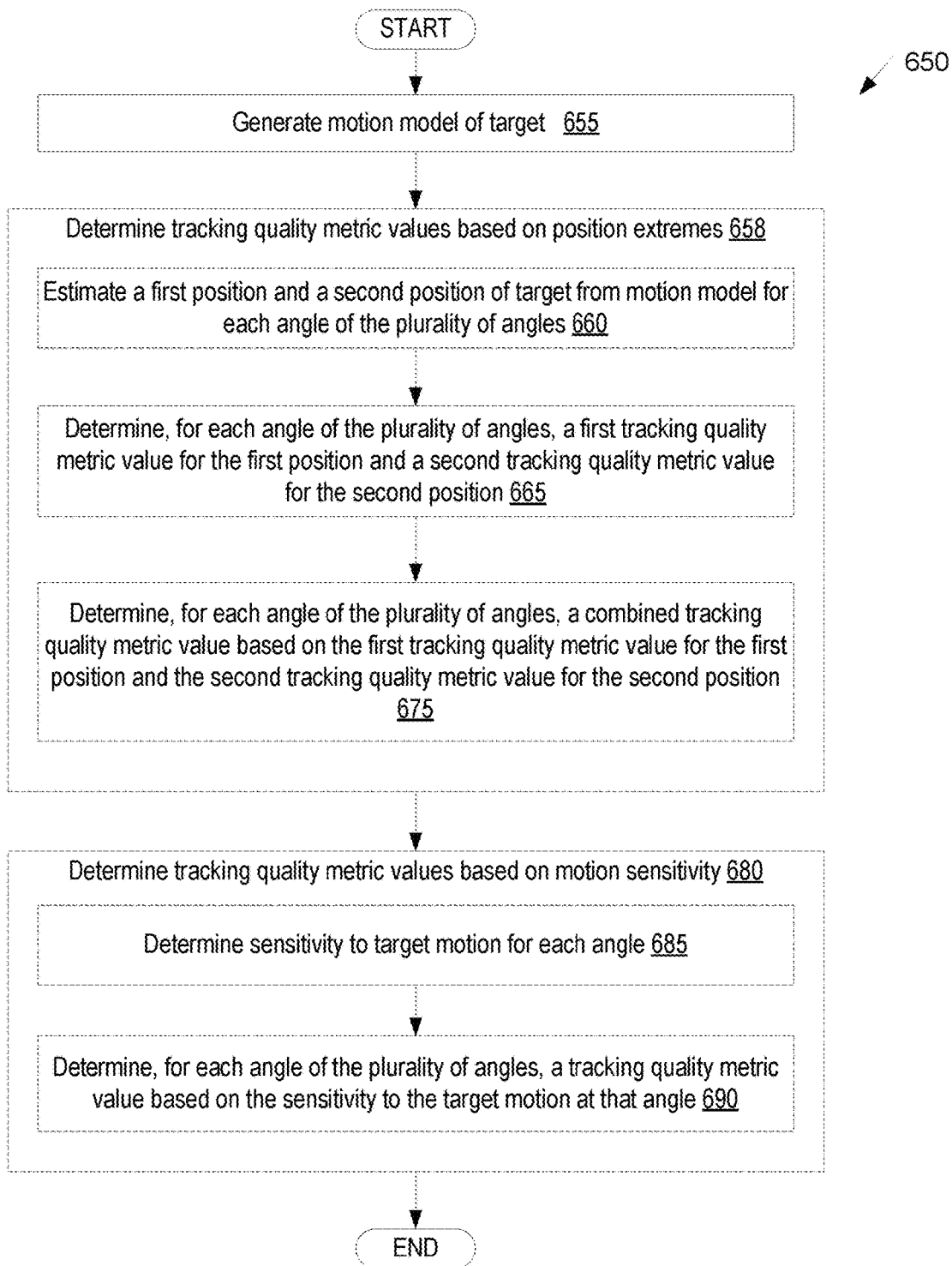
FIG. 6B illustrates a method of determining tracking quality metric values for angles based on a motion model, in accordance with one embodiment of the present invention.

FIG. 6B illustrates a method 650 of determining tracking quality metric values for angles based on a motion model, in accordance with one embodiment of the present invention. Method 650 may be performed, for example, at block 218 of method 200.

At block 655 of method 650, processing logic generates a motion model of a target. The motion model may be for a cyclic motion (e.g., a motion that occurs with breathing) or for a quasi-static motion. The motion model may be generated based on statistical information about how targets of a particular type generally move. For example, a statistical motion model may be generated for prostate motion based on statistical information about how prostates of many patients have been detected to move. The motion model may alternatively or additionally be based on additional information, such as on a 4D CT scan or other 4D treatment planning image of the patient showing motion of the target.

At block 658, processing logic may determine tracking quality metric values for the plurality of angles based on position extremes of the target. In one embodiment, at block 660 processing logic estimates a first position and a second position of the target from the motion model for each angle of the plurality of angles. The first position and the second position may be at two extremes of the motion model. For example, if the motion model is for motion of a target in the lungs, a first position may be at full inhalation and a second position may be at full exhalation.

In one embodiment, at block 665 processing logic determines, for each angle of the plurality of angles, a first tracking quality metric value for the first position and a second tracking quality metric value for the second position. At block 670 processing logic may then determine, for each angle of the plurality of angles, a combined tracking quality metric value based on the first tracking quality metric value for the first position and the second tracking quality metric value for the second position. In one embodiment, the combined tracking quality metric value is an average of the two tracking quality metric values. In one embodiment, the combined tracking quality metric value is maintained as two separate tracking quality metric values, and each of these tracking quality metric values is separately compared against the tracking quality metric criteria.

In one embodiment, at block 680 processing logic determines tracking quality metric values based on motion sensitivity at each of the plurality of angles. In one embodiment, at block 685 processing logic determines a sensitivity to target motion for each angle of the plurality of angles. Determining the motion sensitivity for an angle may include determining an amount of motion that is detectable at that angle. For example, processing logic may determine a principal axis of motion for the target. Those angles that are approximately orthogonal to the principal axis of motion may detect the largest amount of motion for the target. For example, motion of a target that has significant anterior-posterior motion may be most visible in images generated from left and right imaging angles rather than anterior and posterior imaging angles.

At block 690 processing logic may then determine, for each angle of the plurality of angles, a tracking quality metric value based on the sensitivity to the target motion at that angle (e.g., based on the amount of motion that is detectable at that angle). A higher motion sensitivity (higher amount of detectable motion) may indicate that target motion will more likely be captured from an angle during treatment, thus increasing target tracking accuracy. Accordingly, higher motion sensitivity may result in a higher tracking quality metric value.

Numerous different tracking quality metric values and inputs for tracking quality metric values have been discussed herein with reference to FIGS. 2-6B. However, it should be understood that embodiments are not limited to those tracking quality metric values and inputs described herein. These tracking quality metric values and/or inputs for tracking quality metric values may be combined together and/or with other inputs and/or metrics in any combination. For example, input for a tracking quality metric value, which may be used alone or in conjunction with any of the other tracking quality metric value inputs discussed herein, may be based on a field of view (FOV) for a projection associated with an angle. Due to a position of the target with respect to a treatment isocenter, a FOV of a projection for different angles may vary. Larger FOVs provide greater information, and so may be preferable. Accordingly, one tracking quality metric criterion may be a FOV size threshold. If the FOV of a projection associated with a particular angle is below the FOV size threshold, then the tracking quality metric value for that angle may be reduced and/or the tracking quality metric value may fail to satisfy the tracking quality metric criteria.

FIGS. 7-9C are flow charts illustrating various methods of selecting angles for use during an alignment phase and/or a treatment phase of a treatment stage. Accordingly, the methods of FIGS. 7-9C may be used for in-treatment angle selection in embodiments. The methods may be performed by a processing logic that may comprise hardware (e.g., circuitry, dedicated logic, programmable logic, microcode, etc.), software (e.g., instructions run on a processing device to perform hardware simulation), or a combination thereof. The methods of FIGS. 7-9C may be performed by processing logic of a treatment planning system (e.g., treatment planning system 118 of FIG. 1) and/or by processing logic of an IGRT delivery system (e.g., IGRT delivery system 104 of FIG. 1) in embodiments.

Figure 12:
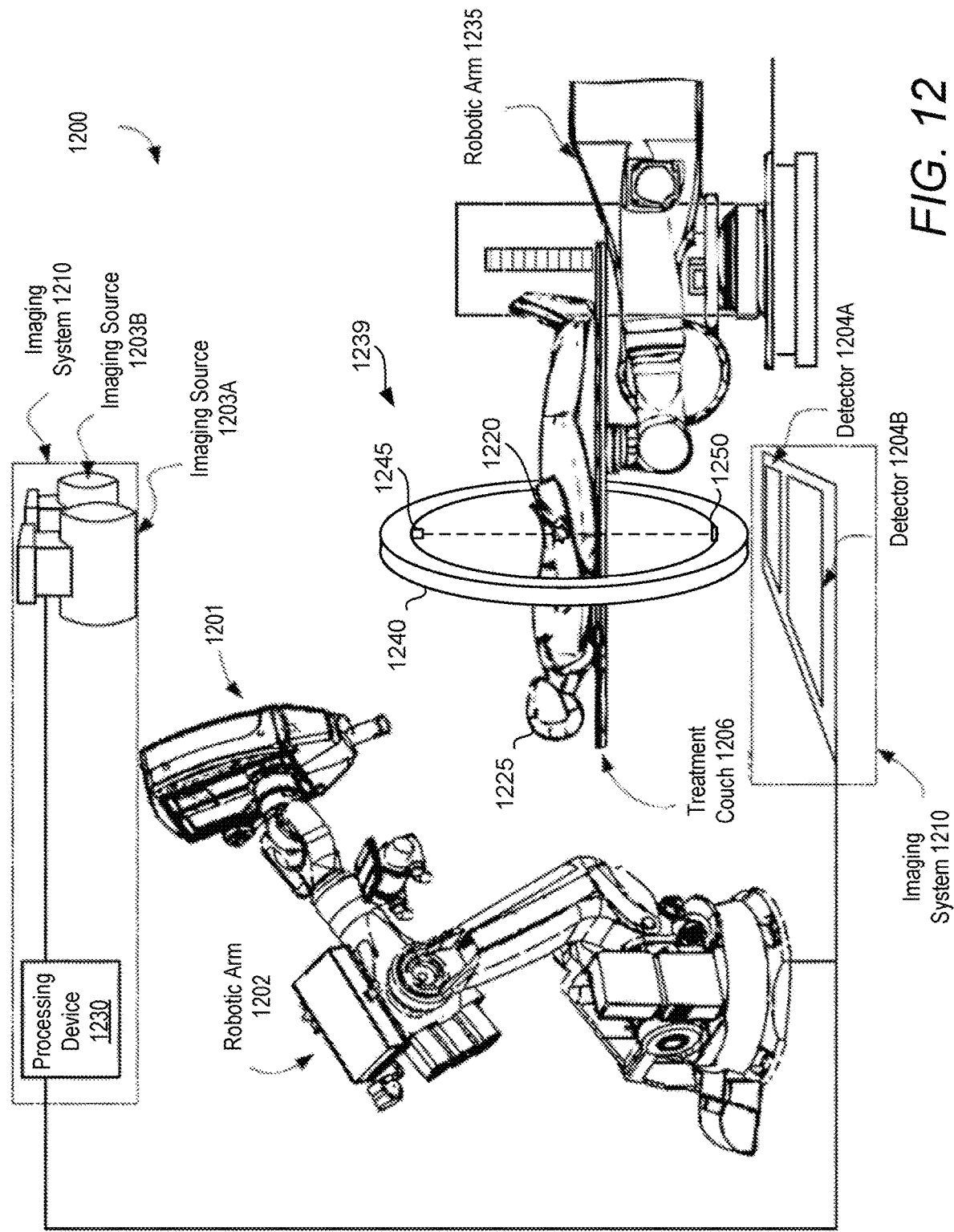
FIG. 12 illustrates a perspective view of a robotic arm based IGRT delivery system, according to a one embodiment.

The methods of FIGS. 7-9C may be performed, for example, by an IGRT delivery system that includes a rotational imaging device that may rotate about a treatment couch (and a patient) by 360 degrees (e.g., in a 360 degree arc). In some embodiments, the rotational imaging device is mounted to a rotatable gantry to which a radiation treatment source is also mounted. In other embodiments, the rotational imaging device is mounted to a rotatable gantry or ring that does not include a radiation treatment source mounted to it. In one embodiment, the IGRT delivery system is a gantry-based IGRT delivery system, such as shown in FIGS. 10A-10C. The gantry-based IGRT delivery system of FIGS. 10A-10C is one type of helical delivery radiation therapy apparatus. For helical delivery radiation therapy apparatuses, a treatment couch holding a patient may move through a rotating gantry to which an imaging device and radiation treatment source are mounted during treatment. In one embodiment, the IGRT delivery system is a robotic arm based IGRT delivery system, such as shown in FIG. 12.

In some implementations, one or more of methods 200-650 may be performed prior to the treatment stage (e.g., during treatment planning) and the methods of one or more of FIGS. 7-9C may be performed for the treatment stage after one or more of methods 200-650 have been performed. Alternatively, the methods of one or more of FIGS. 7-9C may be performed without first performing method 200, for example.

The alignment phase of a treatment stage involves aligning a patient for an IGRT delivery system. The patient may be placed onto a treatment couch, and one or more images may be taken of the patient by an imaging device at various angles. If a motion model is to be used for tracking of a target, the alignment phase may also include generating the motion model based on tracking images taken from the various angles and/or updating a previously generated motion model based on the tracking images. For example, a first series of images of the patient may be taken at a first angle to capture different phases of a cyclic motion from the first angle and a second series of images may be taken at a second angle to capture the different phases of the cyclic motion from the second angle. These images may then be used to generate or update a motion model.

Figure 7:
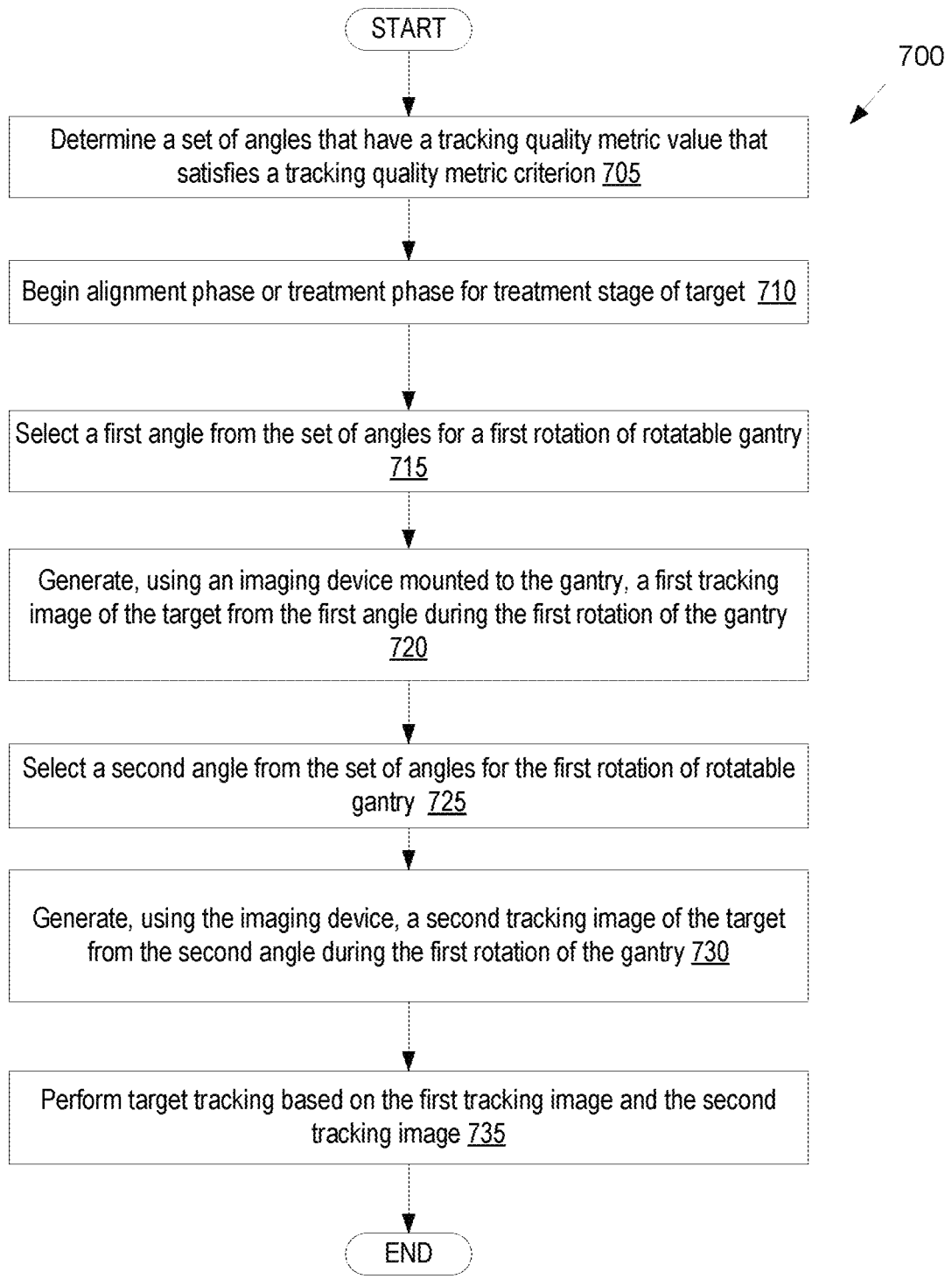
FIG. 7 illustrates a method of selecting a set of angles for use by a rotational imaging device during a treatment stage, in accordance with one embodiment of the present invention.

FIG. 7 illustrates a method 700 of selecting a set of angles for use by a rotational imaging device during an alignment phase or a treatment phase of a treatment stage, in accordance with one embodiment of the present invention.

At block 705 of method 700 processing logic determines a set of angles that have a tracking quality metric value that satisfies tracking quality metric criteria. In one embodiment, one or more of methods 200-650 are performed at block 705 to determine the set of angles. Alternatively, one or more of methods 200-650 may have previously been performed during treatment planning. In such an instance, determining the set of angles may include receiving a list that includes the set of angles and/or reviewing the list. Additionally, or alternatively, the set of angles may be based at least in part on angles that were successfully used in previous treatment stages for the patient. For example, processing logic may build a histogram of angles that have been successfully used during various treatment stages for the patient. This information may be used to adjust the tracking quality metric values for the angles in the set of angles. For example, processing logic may increase the tracking quality metric values for angles that were successfully used in previous treatment stages in some embodiments. Processing logic may favor angles that have been successfully used over other angles from the set of angles in other ways as well.

At block 710, processing logic begins an alignment phase or a treatment phase for a treatment stage (also referred to as a treatment fraction) of a target. Method 700 may be performed during the alignment phase and again during the treatment phase in some embodiments.

At block 715, processing logic selects a first angle from the set of angles for a first rotation of a rotatable gantry to which an imaging device is mounted. In one embodiment, the first angle is an angle from the set of angles having a highest tracking quality metric value. In one embodiment, the first angle is an angle from the set of angles that is within a first angle range (e.g., 30-60 degrees) and that has the highest tracking quality metric value in that angle range. At block 720, the imaging device mounted to the rotatable gantry generates a first tracking image of the target from the first angle during a first rotation of the gantry.

At block 725, processing logic selects a second angle from the set of angles for the first rotation of the rotatable gantry to which the imaging device is mounted. In one embodiment, the second angle is separated from the first angle by at least 15 degrees (e.g., the first angle may be 15 degrees and the second angle may be 30 degrees or more). In a further embodiment, the second angle is separated from the first angle by at least 30 degrees. In a further embodiment, the second angle is separated from the first angle by about 70-110 degrees (e.g., by about 90 degrees in one embodiment). In one embodiment, the second angle has a second highest tracking quality metric value from the set of angles. In one embodiment, the second angle has a highest tracking quality metric value from a subset of the set of angles that are separated from the first angle by at least an angle separation threshold (e.g., by at least 15 degrees, at least 30 degrees, at least 60 degrees, etc.).

At block 730, the imaging device mounted to the rotatable gantry generates a second tracking image of the target from the second angle during the first rotation of the gantry.

At block 735, processing logic may perform target tracking based on the first tracking image and the second tracking image. In some instances, performing target tracking may include generating or updating a motion model for the target using the tracking images. Additional angles may also be selected and used to generate additional tracking images of the target during the first rotation of the rotatable gantry. Additionally, or alternatively, the first and second angles and/or different angles may be used during future rotations of the rotatable gantry to generate additional tracking images. These additional tracking images may be used to continue to track the target. For example, two angles (e.g., optionally separated by about 90 degrees) may be selected and used every rotation of the rotatable gantry. In another example, three angles (e.g., optionally separated by 60 degrees) may be selected and used every rotation of the rotatable gantry. In another example, more than three angles may be selected and used every rotation of the rotatable gantry.

In one embodiment, to perform target tracking processing logic applies a target tracking algorithm that performs image registration between a tracking image taken at an imaging angle and a DRR generated from a corresponding angle of a CT scan or other treatment planning image of the patient. Based on the image registration the target tracking algorithm may determine a location of the target as well as a shape of the target.

In one embodiment, processing logic applies the target tracking algorithm to determine the position of the target in a first reference frame represented by a tracking image, e.g., a live x-ray acquired from the imaging device in a treatment room reference frame, relative to a second reference frame represented by a template of patches selected from a second image, e.g., a DRR, where the location and shape of the target are known or defined in the second reference frame. The template patches are selected based on their perceived ability to distinguish characteristics of the target in the first image from nearby structures. The target's location in the first image is found by computing similarity values between each of several hypothetical, or candidate, locations for the target and the template patches. A maximum value of the similarity values indicates the location of the target in the first image.

A similarity value for a candidate location may be based on a combination of similarity values for each template patch at the candidate location. "Similarity values" or "similarity measures" are numbers that reflect the degree to which two images are similar to each other. For example, a cross-correlation or combination of several cross-correlations between two images can be used to compute a similarity value. This combination of similarity values may be weighted according to the relative importance of the informational content about the target among the template patches. In one embodiment, the similarity value for a candidate location, or template-level similarity value, is a weighted sum of the similarity values of the template patches, or patch-level similarity values, at the candidate location. For example, the weighting applied can be a standard deviation of the pixel values in the patches. As such, patches with a higher standard deviation are given greater weight when computing the template-level similarity value. Other numerical combinations and/or weightings of patch-level similarity values may be used to compute template-level similarity values.

One embodiment for locating a target proceeds by first assembling patch-level similarity maps over a tracking region for each patch. Each patch-level similarity map contains a similarity value for the patch at each of the candidate locations considered in the image. The patch-level similarity maps are then combined, according to their spatial relationship in the template, to produce a global similarity map. The combination of the patch-level similarity maps may be a weighted sum of the similarity values in each patch-level similarity map.

In an alternative embodiment for locating a target, a template-level similarity value for a candidate location is determined before proceeding to the next candidate location. Thus, in this alternative method, patch-level similarity maps are not used. Instead, the candidate locations in the global similarity map are populated with template-level similarity values as the template is moved from one candidate location to another.

Similarity values as described above may be computed using, but not limited to, a cross-correlation, entropy, mutual information, gradient correlation, pattern intensity, gradient difference, or image intensity gradients methods. The computed values may be normalized so that the resulting similarity value is a number ranging between 0 and 1 or −1 and 1.

Figure 8:
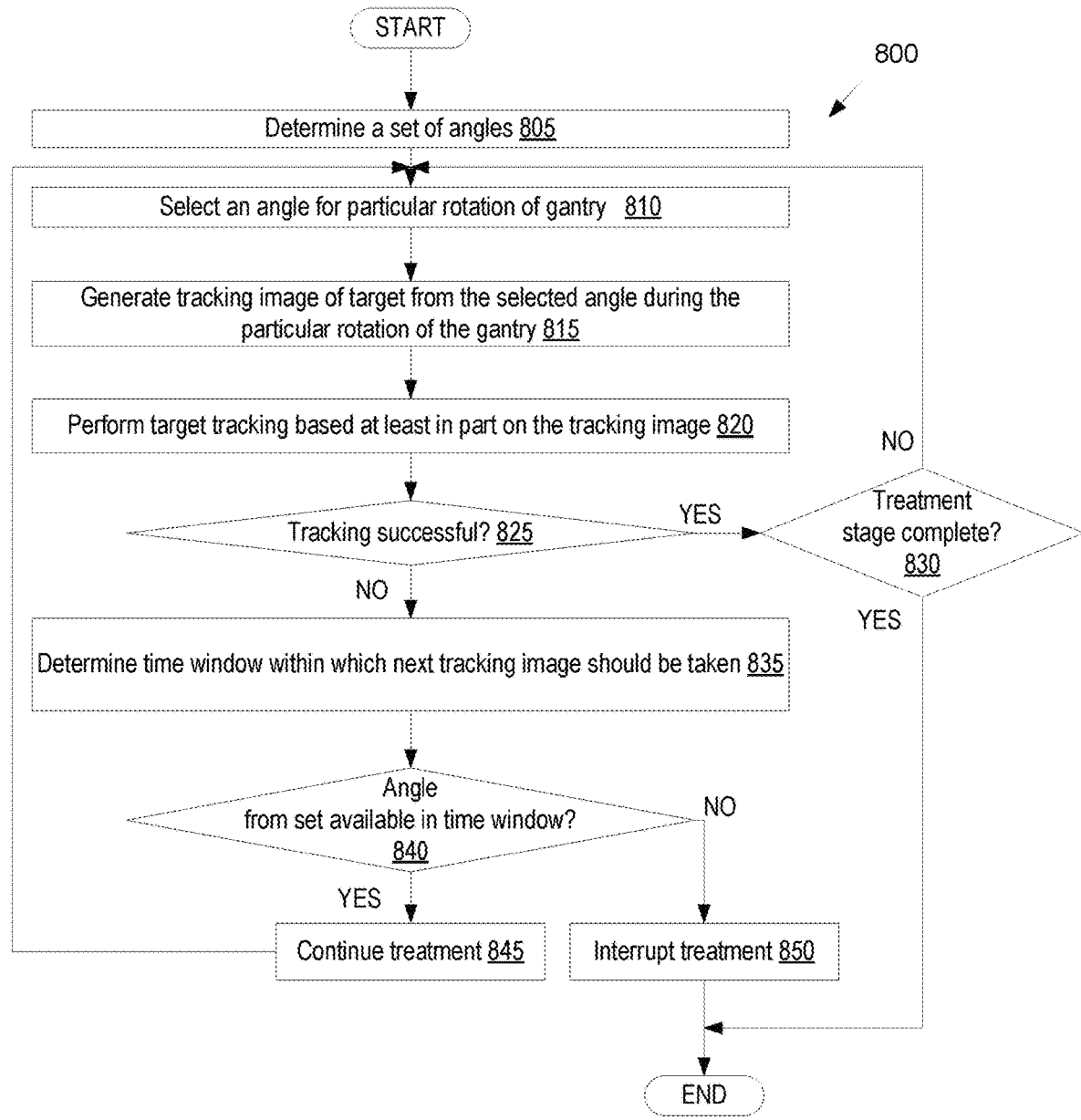
FIG. 8 illustrates a method of using a set of angles by a rotational imaging device during a treatment stage, in accordance with one embodiment of the present invention.

FIG. 8 illustrates a method 800 of using a set of angles by a rotational imaging device during a treatment phase of a treatment stage for patient treatment, in accordance with one embodiment of the present invention. At block 805, processing logic determines a set of angles that are candidates for use during the treatment stage generate tracking images. The set of angles may be determined based on a received list that includes the set of angles (e.g., an ordered list ranking angles from highest tracking quality metric value to lowest tracking quality metric value). Alternatively, or additionally, the set of angles may be determined by performing the operations of one or more of methods 200-650.

At block 810, processing logic selects a first angle from the set of angles for a first rotation of the gantry. The first angle may be an angle having a highest tracking quality metric value, or may be an angle within a rotational range (e.g., from angles 0-90 degrees) having a highest tracking quality metric value. At block 815, processing logic causes an imaging device (e.g., an x-ray source and detector pair) to generate a tracking image of the target from the selected angle during the first rotation of the gantry. At block 820, processing logic attempts to perform target tracking based at least in part on the tracking image. In one embodiment, one or more previous images may already have been taken during the treatment phase and/or during an alignment phase of the treatment stage. In such an instance, the target tracking may be performed based on the first image and the one or more previous images.

At block 825, processing logic determines whether tracking was successful using the first tracking image. Tracking may be successful if the target was successfully identified in the first image. If the tracking was successful, the method continues to block 830.

At block 830, processing logic determines whether the treatment stage is complete. If the treatment stage is complete, the method ends. If the treatment stage is not complete, the method returns to block 810 and another angle is selected and then used to generate another tracking image. The other tracking image may be generated during the first rotation of the rotational gantry or during a subsequent rotation of the rotatable gantry.

If at block 825 it is determined that tracking was not successful, then the method proceeds to block 835. Tracking may be unsuccessful if a target tracking algorithm is unable to identify the target in the tracking image. At block 835, processing logic determines a time window within which a next tracking image should be taken. Target tracking may be performed to update a motion model of the target. If the target tracking is unsuccessful for a most recent tracking image, older tracking images may continue to be relied upon for the motion model. However, over time the accuracy of the motion model may degrade without updated tracking images. The size of the time window may be dependent on how quickly an accuracy of the motion model degrades over time. For example, if a target is susceptible to quasi-static motion, then the motion model's accuracy may degrade quickly. If the target is susceptible to cyclic motion, then the motion model's accuracy may degrade more slowly.

A quasi-static motion model (also referred to as an episodic motion model) models the target as having a static position at its last viewed position. Each time the target is imaged, the target location is updated to a newly observed location, and is then assumed to stay at that location until a new location is detected. A typical imaging time window for a quasi-static motion model may be between about 1-30 seconds, depending on dose delivery rate and other clinical factors such as expected amplitude of episodic motion, expected probability of episodic motion, and distance of treatment target from highly sensitive or at risk organs.

A cyclic motion model (also referred to as a periodic motion model) models the target as continuously moving through a cyclic motion such as caused by breathing or a beating heart. For a cyclic motion model the time window may be on the order of about 5-120 seconds. The time window may vary depending on patient characteristics. For example, the time window may be about 15-60 seconds for some patients, and may be about 90-120 seconds for other patients. In an example, if a patient breathes very regularly, is relaxed, and does not move spontaneously or cough, the motion model may use very minimal adjustments through the entire treatment and may therefore use a window of about 90-120 seconds.

At block 840, processing logic determines whether another angle from the set of angles will be available within the time window. The rotational gantry may rotate at a predetermined speed. For example, the rotatable gantry may rotate at a speed of 2 rotations per minute, 5 rotations per minute, 10 rotations per minute, 15 rotations per minute, 20 rotations per minute, or faster. The number of available angles from the set of angles may vary on the speed of rotation and the size of the time window.

Assume for an example that the time window is 2 seconds, that the imaging device is at angle 5 degrees when the tracking fails for a most current tracking image, that the rotational gantry rotates at a speed of 5 rotations per minute, and that a next angle in the set of angles is at 38 degrees. At a rotational speed of 5 rotations per minute, the rotational gantry is rotating 30 degrees every second. Accordingly, the next angle in the set of angles at 38 degrees will be available within the time window. If, on the other hand, the next angle was at 80 degrees, the next angle would be outside of the time window. If an angle is available in the time window, the method continues to block 845 and at block 845 treatment is continued and the method returns to block 810 to select another angle. Otherwise the method proceeds to block 850.

In many instances multiple angles will be available within the time window. For example, at a rotational speed of 10 rotations per minute the imaging devices sweeps all 360 degrees every 6 seconds. Accordingly, at that rotational speed a time window of 6 seconds would cause all angles from the set of angles to be available. If multiple angles are available, processing logic selects one of the available angles that are available within the time window at block 810. In one embodiment, an angle with a highest tracking quality metric value is selected. In one embodiment, a next in time angle is selected. In one embodiment, a next angle is selected based on a combination of when each of the angles will be available and the tracking quality metrics of those angles. In one embodiment, an angle of a last tracking image in which the target was successfully tracked is also taken into consideration. For example, it may be preferable to select an angle that is 90 degrees apart from the angle of the last successful tracking image. In some embodiments multiple previous tracking images are taken into consideration for selection of a next imaging angle. For example, if there are images covering most patient breathing phases, the system may select a next image that will be taken at an angle that will correspond to a breathing phase for which a recent image has not been generated.

At block 850 treatment is interrupted. This may include stopping rotation of the rotatable gantry and/or stopping delivery of a radiation treatment beam. During the interruption one or more additional tracking images of the target may be generated until the target is successfully located. Additionally, a motion model of the target may be updated. The treatment may then continue and the method may resume from block 810.

Figure 9A:
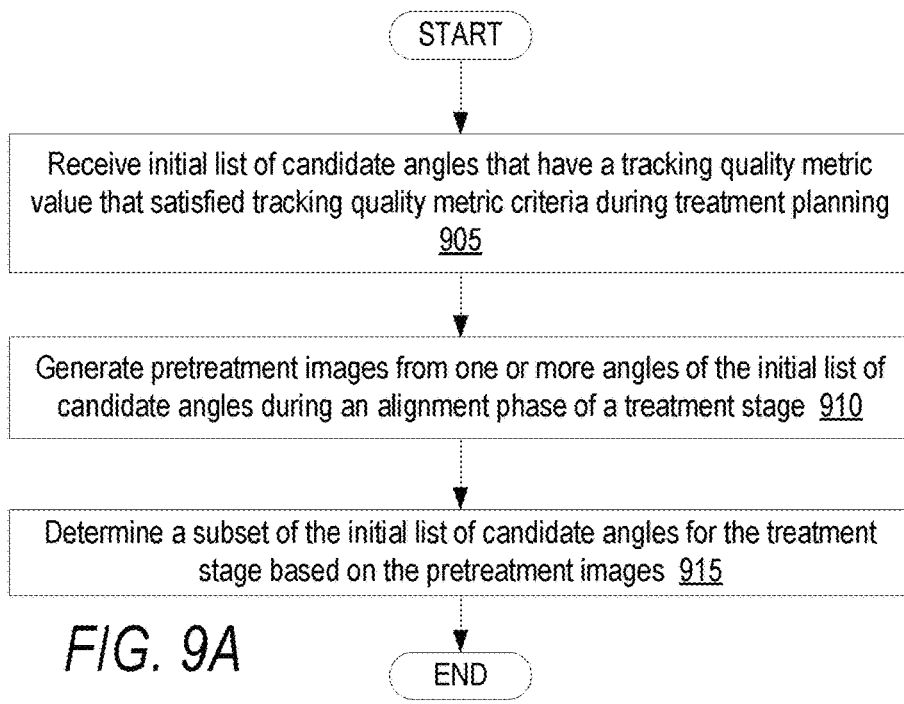
FIG. 9A illustrates a first method of selecting a set of angles for use by a rotational imaging device during a treatment stage, in accordance with one embodiment of the present invention.
Figure 9B:
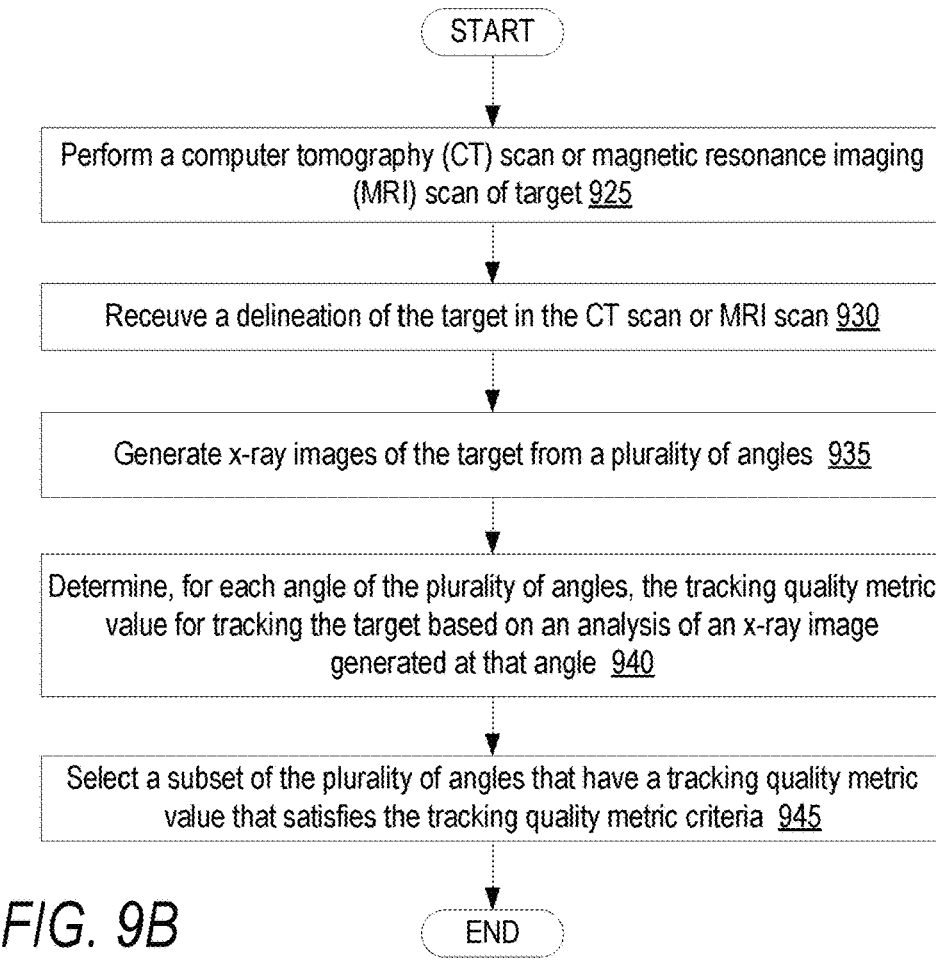
FIG. 9B illustrates a second method of selecting a set of angles for use by a rotational imaging device during a treatment stage, in accordance with one embodiment of the present invention.
Figure 9C:
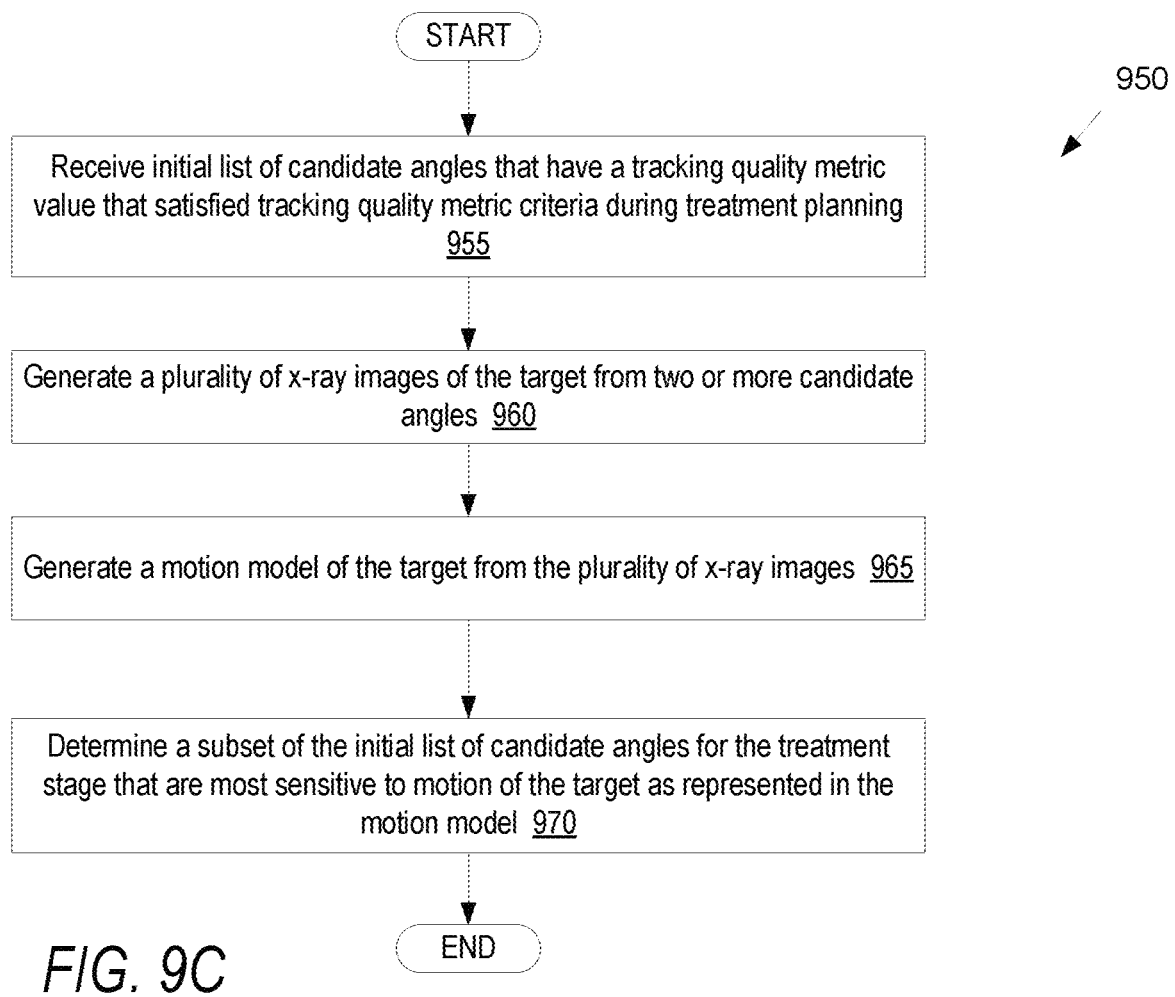
FIG. 9C illustrates a third method of selecting a set of angles for use by a rotational imaging device during a treatment stage, in accordance with one embodiment of the present invention.
Figures 10A, 10B:
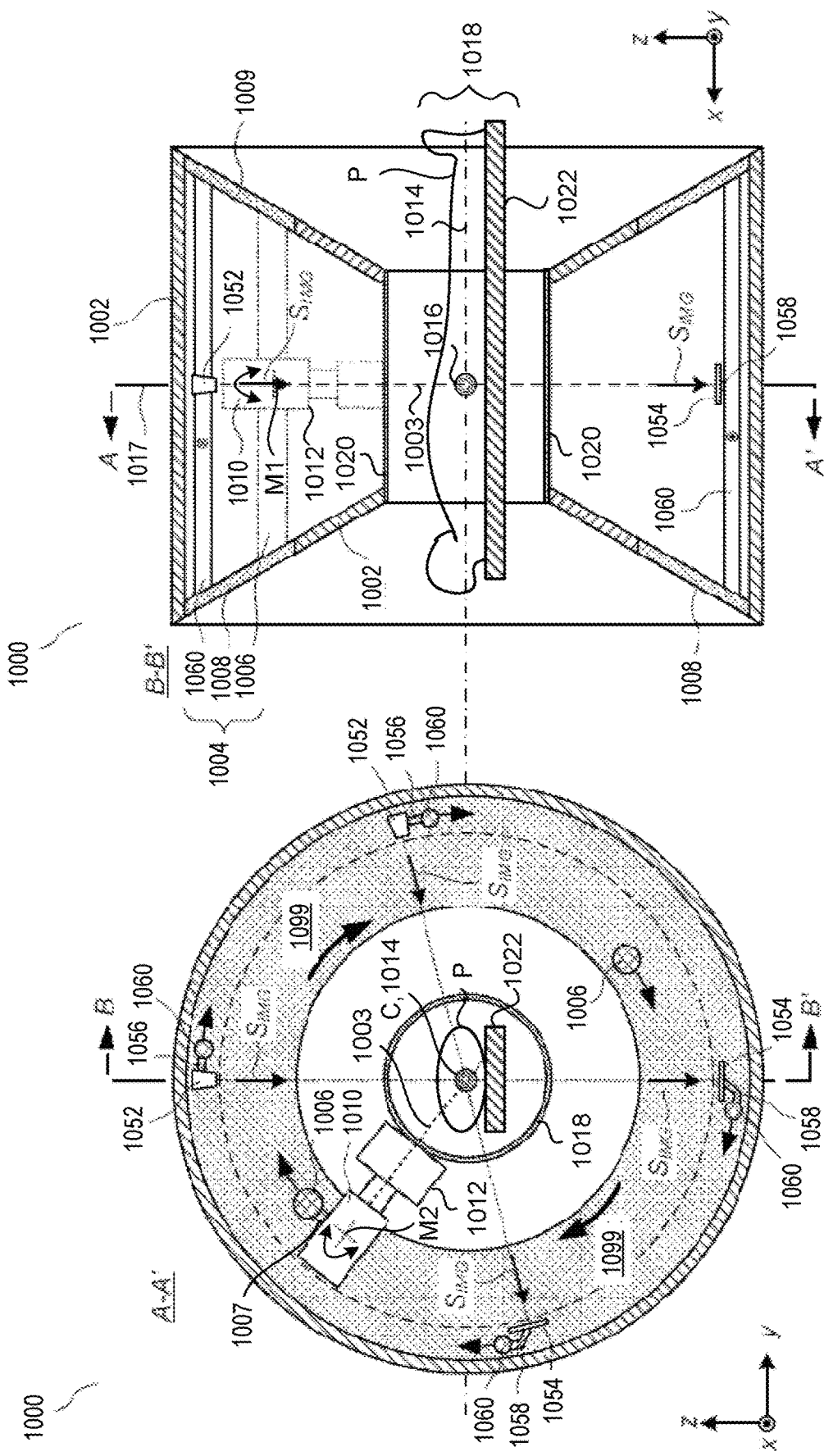
FIG. 10A illustrates an axial cut-away view of a gantry based image-guided radiation treatment (IGRT) system according to a one embodiment.
FIG. 10B illustrates a side cut-away views of the gantry based IGRT delivery system of FIG. 10A, according to one embodiment.
Figure 10C:
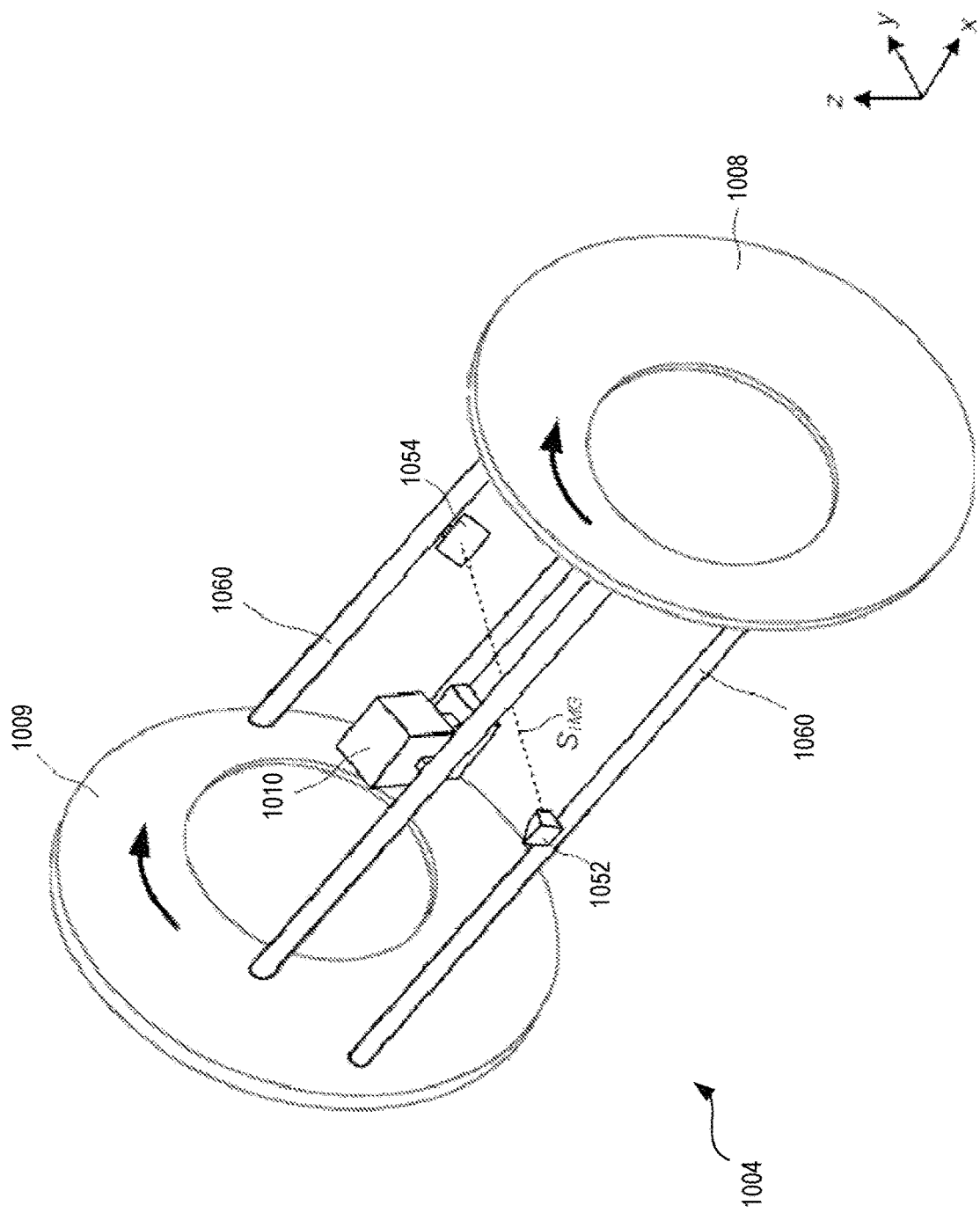
FIG. 10C illustrates a perspective view of a rotatable gantry structure of the IGRT delivery system of FIGS. 10A-10B, according to one embodiment.

FIGS. 9A-9C illustrate various methods of selecting a set of angles from which tracking images may be taken. These methods may be used alone or in combination at block 805 of method 800 and/or at block 705 of method 700.

FIG. 9A illustrates a first method 900 of selecting a set of angles for use by a rotational imaging device during a treatment stage, in accordance with one embodiment of the present invention. At block 905 of method 900, processing logic receives an initial list of candidate angles that have tracking quality metric values that satisfied one or more tracking quality metric criteria during treatment planning. At block 910, processing logic causes an imaging device to generate pretreatment images of a target from one or more angles of the initial list of candidate angles. These pretreatment images may be generated during an alignment phase of a treatment stage. At block 915, processing logic determines a subset of the initial list of candidate angles for the treatment stage based on the pretreatment images. For example, processing logic may sample 10%-50% of the candidate angles and update tracking quality metric values for those sampled angles. Processing logic may additionally interpolate changes to the non-sampled angles based on the changes to the sampled angles.

FIG. 9B illustrates a second method 920 of selecting a set of angles for use by a rotational imaging device during a treatment stage, in accordance with one embodiment of the present invention. At block 925 of method 900, processing logic performs a CT scan or MRI scan of a target in a patient. At block 930, processing logic receives a delineation of the target in the CT scan or MRI scan.

At block 935, processing logic generates x-ray images of the target from a plurality of angles. At block 940, processing logic determines, for each angle of the plurality of angles, the tracking quality metric value for tracking the target based on an analysis of an x-ray image generated at that angle. The tracking quality metric value may be determined using any of the aforementioned techniques, except that an x-ray is used rather than a standard DRR to generate the tracking quality metric value. At block 945, processing logic then selects a subset of the plurality of angles that have a tracking quality metric value that satisfies the one or more tracking quality metric criteria.

FIG. 9C illustrates a third method 950 of selecting a set of angles for use by a rotational imaging device during a treatment stage, in accordance with one embodiment of the present invention. At block 955 of method 950 processing logic receives an initial list of candidate angles that have a tracking quality metric value that satisfied one or more tracking quality metric criteria during treatment planning. At block 960, processing logic generates a plurality of x-ray images of the target from two or more candidate angles. At block 965, processing logic generates a motion model of the target from the plurality of images. The motion model may also be based at least in part on a general statistical motion model that describes how a particular type of target is likely to move over time in some embodiments. At block 970, processing logic determines, for each angle in the list of candidate angles, a motion sensitivity at that angle. Processing logic then determines a subset of the initial list of candidate angles for the treatment stage that are most sensitive to motion of the target as represented in the motion model.

FIGS. 10A-10C illustrate an IGRT delivery system 1000 that is capable of carrying out the functionalities described above with respect to the IGRT delivery system 104 of FIG. 1 according to one or more embodiments. The IGRT delivery system 1000 may be the IGRT delivery system referred to in methods 200-950 in various embodiments. FIG. 10A illustrates an axial cut-away view of the gantry based image-guided radiation treatment (IGRT) system 100 according to one embodiment. FIG. 10B illustrates a side cut-away view of the gantry based IGRT delivery system 1000, according to one embodiment. FIG. 10C illustrates a perspective view of the rotatable gantry structure of the IGRT delivery system 1000, according to one embodiment.

IGRT delivery system 1000 includes a gantry frame 1002 within which is disposed a rotatable gantry structure 1004 configured to rotate around a rotation axis 1014 that passes through an isocenter 1016. In the illustrated example, the rotatable gantry structure 1004 rotates in the clockwise direction 1099. However, the rotatable gantry structure may also rotate in a counter-clockwise direction. Associated with the IGRT delivery system 1000 is an imaginary plane, termed herein a transverse isocentric plane 1017, that is orthogonal to the rotation axis 1014 and passes through the isocenter 1016. The gantry frame 1002, the isocenter 1016, the rotation axis 1014, and the transverse isocentric plane 1017 may be fixed and motionless relative to a treatment vault (not shown) in which the IGRT delivery system 1000 is installed. As used herein, an isocenter or machine isocenter is a physical point in a treatment room (treatment vault). A treatment center is a point within the target volume defined by a physician during treatment planning, normally based within the pretreatment treatment planning image reference frame (e.g., pretreatment CT image reference frame). For isocentric treatment the treatment center may be aligned with the machine isocenter during the set up procedure described above.

The rotatable gantry structure 1004 includes one or more beam members 1006 that each extend between first ring member 1008 and second ring member 1009 disposed approximately on opposite sides of the transverse isocentric plane 1017. Note that the two ends of a beam member may or may not be 180 degrees apart. By offsetting the source and detector, a field of view may be increased. The first ring member 1008 corresponds generally to a first end of the rotatable gantry structure 1004 (toward the left side of FIG. 10B), while the second ring member 1009 corresponds generally to a second, opposite end of the rotatable gantry structure 1004 (toward the right side of FIG. 10B). The first and second ring members 1008 and 1009 are supported at their respective ends of the rotatable gantry structure 1004 by corresponding ends of the gantry frame 1002 in a manner that allows and facilitates rotation of the rotatable gantry structure 1004 around the rotation axis 1014 while keeping the rotation axis 1014 highly stable and stationary. The skilled artisan will appreciate that any of a variety of different mechanical support schemes that allow such rotation can be used (e.g., anti-friction sleeves, slip bearings, roller bearings, etc.). The skilled artisan will appreciate that the gantry frame 1002 can be made substantially thicker or otherwise reinforced at its respective ends than is indicated schematically in FIG. 10B, in accordance with the particular materials being used and other design considerations, for ensuring such mechanical stability.

The rotatable gantry structure 1004 may contain two beam members 1006 separated by approximately 180 degrees around the rotation axis 1014, which is useful (for example and without limitation) for facilitating rotational balancing (e.g. by applying appropriate balancing weights to the opposing beam members 1006). The skilled artisan will appreciate that the term beam member as used herein can encompass a wide variety of different types of structural members (e.g., solid rods, hollow rods, assemblies of parallel or concentric rods, truss-type structures, etc.) that can structurally extend from one place to another and along which one or more physical items (e.g., LINACs, LINAC assemblies, imaging sources, imaging detectors, and so forth) can be fixably or movably mounted or positioned.

Movably mounted on one of the beam members 1006 is a radiation treatment source 1010 (also referred to as a therapeutic radiation head), such as and without limitation a linear accelerator (LINAC) or a compact proton source, which includes thereon an end collimator 1012, such as a multi-leaf collimator (MLC), and which provides a therapeutic radiation beam 1003. The radiation treatment source 1010 is mounted to the beam member 1006 by a coupling device 1007 that is configured and adapted to achieve the translational and rotational functionalities described further hereinbelow.

In one embodiment, the radiation treatment source 1010 comprises a compact lightweight LINAC, such as an X-band or C-band LINAC in a compact configuration without a bending magnet. This allows a compact system design in which all moving components are behind a fixed surface covering (e.g., a bore shield), thus eliminating the risk of collision with the patient and enabling higher rotation speeds. In other alternative embodiment, the compact accelerator can include a bending magnet.

The radiation treatment source 1010 could be a LINAC configured with different secondary collimation systems 1012, including fixed cones, a variable aperture collimator such as the Iris Variable Aperture Collimator (Accuray Incorporated, Sunnyvale, Calif.), a binary collimator, or an MLC.

The rotatable gantry structure 1004 and radiation treatment source 1010 are dimensioned so as to allow a central bore 1018 to exist. The central bore 1018 may be an opening sufficient to allow a patient P to be positioned therethrough without the possibility of being incidentally contacted by the radiation treatment source 1010 or other mechanical components as the gantry rotates radiation head 1010 about patient P. A treatment couch 1022 is provided for supporting the patient P. The treatment couch 1022 may be coupled to an automated patient positioning system (not shown) for moving the patient P into a therapy position and manipulating the patient with three or more degrees of freedom (e.g., three orthogonal translations, one parallel to the rotation axis 1014, two orthogonal to rotation axis 1014, plus optionally one or more rotations). The skilled artisan will appreciate that many couches can be used in accordance with embodiments of the present invention.

According to one embodiment, a cylindrically shaped bore shield 1020 is provided to line the boundary of the central bore 1018. In addition to preventing unexpected movement of the patient's hands or other body part into collision with moving parts, the bore shield 1020 can reduce the sense of intimidation that the patient might feel in view of the large moving parts in the device. The bore shield 1020 provides the ability to maximize the rotation speed of the gantry, while still meeting all regulatory safety requirements. The bore shield 1020 should be formed of a material that is substantially transparent to the therapeutic and imaging radiation, and optionally can be visibly opaque as well.

According to one embodiment, the radiation treatment source 1010 is mounted to the beam member 1006 in a manner that allows and facilitates (i) translation of the radiation treatment source 1010 along the beam member 1006 (i.e., in an end-to-end manner between first ring member 1008 and second ring member 1009), (ii) pivoting of the radiation treatment source 1010 around a first pivot axis M1, termed herein a primary pivot axis, and (iii) pivoting of the radiation treatment source 1010 around a second axis M2, termed herein a secondary pivot axis, located at a right angle to M1. Preferably, the axes M1 and M2 each pass through the center of mass (CoM) of the radiation treatment source 1010, and the center of mass lies along the axis of the therapeutic radiation beam 1003. Collectively, the primary pivoting around axis M1 and the secondary pivoting around axis M2 can be considered as a gimbal or gimballing motion of the radiation treatment source 1010.

The skilled artisan will appreciate that the IGRT delivery system 1000 further includes a plurality of actuators of various types (not shown) for achieving the mechanical functionalities described hereinabove and hereinbelow in the instant disclosure. Thus, for example, the IGRT delivery system 1000 includes respective actuation devices (not shown) to achieve the rotation of the rotatable gantry structure 1004 around the rotation axis 1014, the axial translation of the radiation treatment source 1010 along the beam member 1006, the M1 pivoting of the radiation treatment source 1010, and the M2 pivoting of the radiation treatment source 1010. The IGRT delivery system 1000 further includes one or more processing devices and/or control units, such as may be implemented on one or more programmable computers, for controlling the various actuators and sending signals to and from the various recited radiation sources and detectors as necessary to achieve the functionalities described hereinabove and hereinbelow in the instant disclosure.

Advantageously, by virtue of the possibilities provided by the combination of axial translation of the radiation treatment source 1010, M1 pivoting, and M2 pivoting, a rich variety of radiation treatment delivery plans are facilitated by the IGRT delivery system 1000, as discussed herein. At the same time, by virtue of a ring-style mechanical nature of the rotatable gantry structure 1004 (which could be more particularly referenced as a "barrel-style" mechanical nature), a greater degree of mechanical stability may be provided in comparison to approaches in which radiation treatment source support is of a cantilever-like nature. Generally speaking, in addition to positively affecting the range of achievable tilt angles (i.e., the angle between the therapeutic radiation beam 1003 and the transverse isocentric plane 1017 when the therapeutic radiation beam is isocentric), increased end-to-end distance between the ring members will have an impact on the mechanical stability of the device.

The phrases "rotating the gantry" or "gantry rotation" refer to rotation of the rotatable gantry structure 1004. Advantageously, there are many possible modes of operation for the IGRT delivery system 1000. The rotatable gantry structure 1004 (and thus the radiation treatment source 1010 mounted thereto) may continuously rotate during treatment. Alternatively, the rotatable gantry structure 1004 may be rotated to and parked at a particular angle. The radiation treatment source 1010 can rotate about the patient without tilting off axis. In this case it could treat at a discrete set of fixed gantry rotation angles (coplanar beams) with or without irregular field shaping and with or without modulation, thus enabling coplanar static beams, CRT, and IMRT. For each fixed gantry rotation angle, the radiation treatment source 1010 can be tilted off axis at a tilt angle, thus enabling non-coplanar CRT and IMRT. Alternatively, the radiation treatment source 1010 could be configured with a binary collimator or an MLC and deliver radiation while continuously rotating without tilting off axis. By combining the radiation treatment source 1010 rotation with patient movement through the central bore 1018, which can be accomplished for example by linear translation of the treatment couch 1022, sequential or helical TomoTherapy is enabled. Alternatively, the radiation treatment source 1010 could be configured with a MLC and deliver radiation while rotating the gantry without tilting off axis.

The gantry rotation speed, dose rate, MLC shapes, and collimator angle could be varied during gantry rotation, thus also enabling conventional coplanar rotational arc therapy. By also tilting the radiation treatment source 1010 off axis as the gantry angle is varied, it is possible to deliver rotational arc therapy with multiple non-coplanar rotations in order to maximize the number of beam positions, the solid angle covered by these positions, and the degree of intensity or fluence modulation in order to achieve the highest possible treatment plan quality. In one approach, the tilt angle is held constant while the gantry angle is varied. In another approach, the tilt angle is varied while the gantry angle is also varied (referred to as conical non-coplanar rotational arc therapy and cono-helical rotational arc therapy). This approach could be combined with movement of the treatment couch 1022 during gantry rotation to provide what is termed herein conical non-coplanar tomotherapy or cono-helical non-coplanar tomotherapy. Because of the ability to achieve many orientations using gantry rotation (between 0 and 360 degrees) and moving the source out of plane by varying the tilt angle (within the maximum limits of the system, which could for example be −30 to +30 degrees, or −45 to +45 degrees), breast treatments with parallel opposed fields could be easily and quickly performed by setting the appropriate gantry rotation and tilt angles.

The rotatable gantry structure 1004 is further provided with additional beam members 1060 extending between ring members 1008 and 1009. The additional beam members 1060 are each provided with one (or more) imaging devices (e.g., kV source(s)) 1052 and/or one (or more) imaging detectors (e.g., kV detectors) 1054, and are configured such that each imaging device 1052 is paired with an associated imaging detector 1054 approximately opposite the isocenter. Each imaging device 1052 is coupled to its respective beam member 1006 by a respective coupling device 1056, and each imaging detector 1054 is coupled to its respective beam member 1006 by a respective coupling device 1058, the coupling devices 1056 and 1058 being configured and adapted to achieve the functionalities (e.g., fixed, translational, and/or rotational) described further herein. The beam members 1060 are disposed at suitable angles relative to each other and to the radiation treatment source 1010 to achieve the desired imaging functionality, which can include standard x-ray imaging or stereoscopic imaging when combined with rotation of the imaging device about the patient. In one embodiment, the imaging devices 1052 are mounted orthogonally to the radiation head 1010 on the gantry. This enables the imaging devices 1052 to generate images of a target while the radiation treatment source 1010 delivers a radiation beam to the target.

With one or more imaging device 1052, the system can acquire X-ray images during gantry rotation. Because of the ability to achieve any orientation defined by a gantry rotation angle and a tilt angle, all rotation offsets can be handled by adjusting the rotation and tilt angles appropriately. Two imaging devices 1052 are shown. However, it should be understood that the IGRT delivery system 1000 may instead include a single imaging device 1052. With two or more kV imaging systems, the system can acquire stereo x-ray images simultaneously at any gantry rotation angle. With one kV imaging system, the system can acquire stereo x-ray images non-simultaneously at different gantry rotation angles (separated for example by 90 degrees). X-ray images can be used for patient set up for example by registration of the x-ray images to digitally reconstructed radiographs (DRRs) generated from the planning CT image. If two imaging devices 1052 are used, the imaging devices 1052 may be mounted approximately perpendicular to each other.

The ability to generate intra-treatment images allows for intra-fraction (e.g., in-treatment) target motion tracking. Intra-fraction motion tracking and correction helps enable better treatment plans and the accurate delivery of those treatment plans. A system for correlating target motion with motion of an anatomical feature of the body (for example and without limitation external chest wall or a moving boney structure) can also be included in embodiments of the present invention. For example, a lung tumor will move periodically with respiration, and the tumor location can be correlated with (for example and without limitation) motion of the chest wall as the patient breathes.

Figure 11:
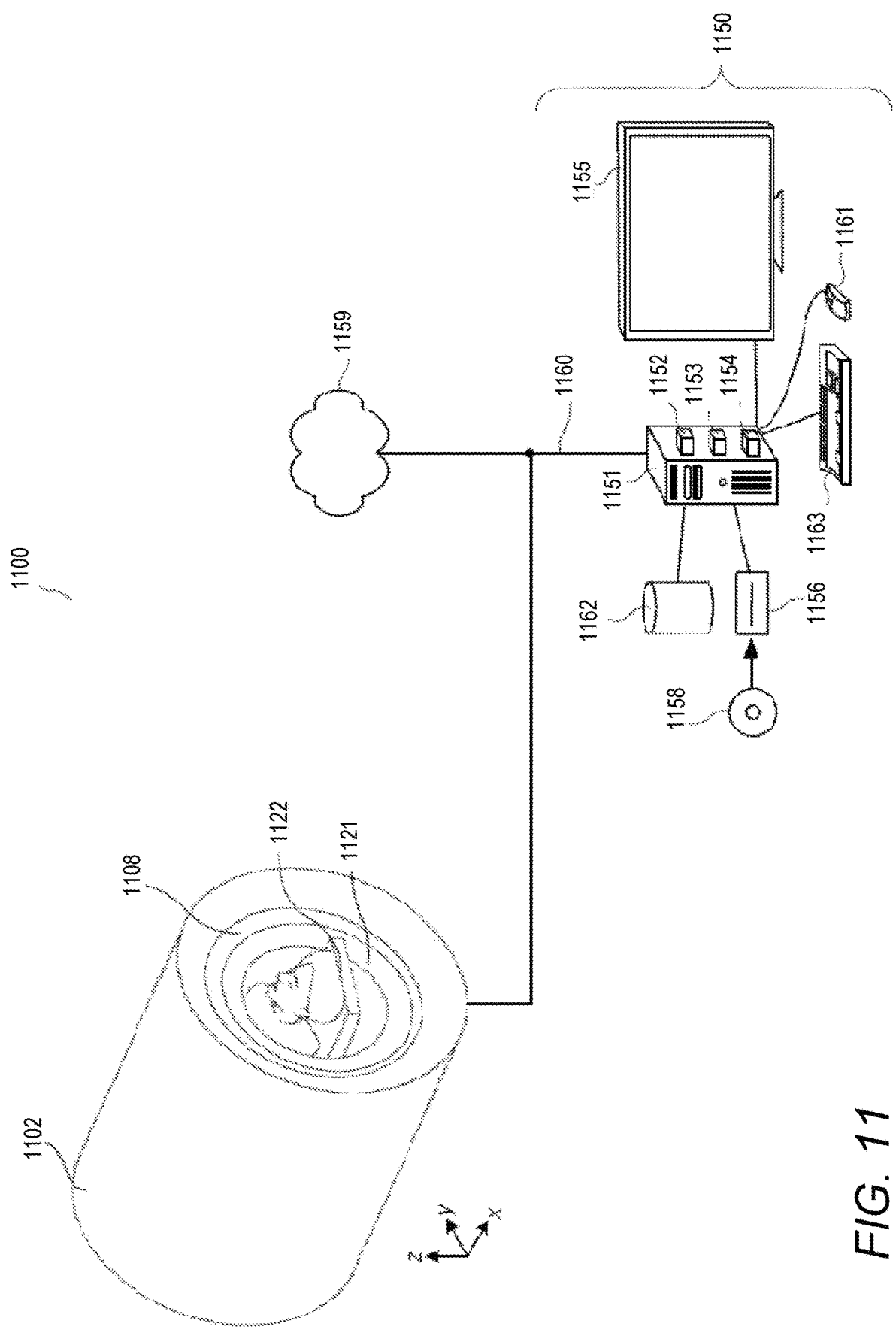
FIG. 11 illustrates a perspective view of a gantry based IGRT delivery system and a schematic diagram of a computer system integral therewith and/or coupled thereto, according to one embodiment.

FIG. 11 illustrates a perspective view of a gantry based IGRT delivery system 1100 and a schematic diagram of a computer system 1150 integral therewith and/or coupled thereto, according to one embodiment. Computer system 1050 uses one or more busses, networks, or other communications systems 1160, including wired and/or wireless communications systems. Computer system 1150 can operate in conjunction with the the IGRT delivery system 1100 to implement the methods of one or more of the embodiments described herein. Methods of image guided radiation treatment in accordance with one or more of the embodiments may be implemented in machine readable code (i.e., software or computer program product) and performed on computer systems such as, but not limited to, the computer system 1150. Computer system 1150 may include a processing device (e.g., a general purpose or special purpose processing device) 1152, random access memory 1153, and nonvolatile memory 1154 (e.g., electromechanical hard drive, solid state drive, etc.). Computer system 1150 may also include various input/output devices, such as a display monitor 1155, a mouse 1161, a keyboard 1163, and other I/O devices 1156 capable of reading and writing data and instructions from non-transitory computer readable storage media 1158 such as tape, compact disk (CD), digital versatile disk (DVD), blu-ray disk (BD), memory, a hard disk drive, and so forth.

In addition, there may be connections via the one or more busses, networks, or other communications systems 1160 to other computers and devices, such as may exist on a network of such devices, e.g., the Internet 1159. Software to control the image guided radiation treatment operations described herein may be implemented as a program product and stored on a tangible storage device such as the non-transitory computer readable storage medium 1158, an external nonvolatile memory device 1162, or other tangible storage medium.

The gantry based IGRTs 1000, 1100 may be used for coplanar rotational arc therapy as well as for non-coplanar rotational arc therapy (e.g., helical delivery). In one embodiment, conical non-coplanar rotational arc therapy may be performed by the gantry based IGRTs 1000, 1100. For conical non-coplanar rotational arch therapy, the radiation treatment source 1010 is axially translated along the beam member 1006 in discrete steps, with a gantry rotation occurring at each step. There can be discrete firings of the therapeutic radiation beam at respective discrete gantry angles, or there can be continuous firings of the therapeutic radiation beam as the gantry angle is continuously changed, each of which are within the scope of the present teachings. In one embodiment, cono-helical non-coplanar rotational arc therapy and other types of helical rotational arc therapy may be performed by the gantry based IGRTs 1000, 1100. For cono-helical non-coplanar rotational arc therapy, the radiation treatment source 1010 is translated along the beam member 1006 as the gantry is rotated. There can be discrete firings of the therapeutic radiation beam at respective discrete gantry angles (and correspondingly discrete translational advances of the radiation treatment source 1010), or there can be continuous firings of the therapeutic radiation beam as the gantry angle is continuously changed (and correspondingly continuous translational advances of the radiation treatment source 1010), each of which are within the scope of the present teachings. Cono-helical non-coplanar rotational arc therapy may span the same conical three-dimensional volume as conical non-coplanar rotational arc therapy, but does so in a continuous or helical manner.

A rich variety of radiation therapy profiles and strategies can be accommodated using the gantry based IGRT delivery systems 1000, 1100. Such possibilities include, but are not limited to: single or parallel opposed static beams with rectangular field shaping and 1D (wedge or virtual wedge using MLC) intensity modulation; static beams with rectangular field shaping and 1D modulation; coplanar rotational treatments ("arc therapy") with rectangular field shaping and 1D modulation; coplanar or non-coplanar beams with irregular field shaping and 1D modulation ("conformal radiation therapy" or CRT); coplanar or non-coplanar beams with irregular field shaping and 2D modulation ("intensity modulated radiation therapy" or IMRT); and tomotherapy (helical or sequential) with coplanar rotation using a narrow beam in combination with couch movement and 2D modulation. Such possibilities further include rotational arc therapy, also called intensity modulated arc therapy (IMAT), including one or more coplanar rotations, irregular field shaping, and 2D modulation, with gantry rotation speed, dose rate, MLC positions, and in some cases collimator angles being varied during rotation, and including multiple rotations that increase the achievable degree of intensity modulation in view of practical constraints on MLC motion during treatment.

One of the benefits of the gantry based IGRT delivery systems 1000, 1100 is achieving rotational arc therapy with multiple non-coplanar rotations in order to maximize the number of beam positions, the solid angle covered by these positions, and the degree of intensity or fluence modulation of the therapeutic radiation beam in order to achieve the highest possible treatment plan quality. The gantry based IGRT delivery systems 1000, 1100 may rotate the gantry at a rate of anywhere from 1-50 rotations per minute or faster in embodiments. In some embodiments the gantry may alternatively be rotated slower than 1 rotation per minute. In one embodiment, the gantry is rotated at a rate of 1-10 rotations per minute. In one embodiment, the gantry is rotated at a rate of about 3-6 rotations per minute. The faster the rotation of the gantry, the greater the freedom to select imaging angles. For example, if the gantry doubles its rotational speed, then the number of good imaging angles needed to provide the same temporal sampling is halved. In one embodiment, the gantry is rotated at a rate of about 5 rotations per minute. Another of the benefits of the gantry based IGRT delivery systems 1000, 1100 is accurate delivery of treatment plans using image guidance for patient set up and intra-fraction motion tracking and correction. Another of the benefits of the gantry based IGRT delivery systems 1000, 1100 is increased rigidity, which enables higher rotation speeds, higher delivery accuracy (less error in radiation beam position and orientation), and higher 3D reconstructed image quality (less error in imaging system geometry during rotation).

FIG. 12 illustrates a perspective view of a robotic arm based IGRT delivery system 1200, according to a one embodiment. In the illustrated embodiment, the IGRT delivery system 1200 includes a linear accelerator (LINAC) 1201 that acts as a radiation treatment source. The LINAC 1201 is mounted on the end of a robotic arm 1202 having multiple (e.g., 5 or more) degrees of freedom in order to position the LINAC 1201 to irradiate a pathological anatomy (e.g., target 1220) with beams delivered from many angles, in many planes, in an operating volume around a patient. Treatment may involve beam paths with a single isocenter, multiple isocenters, or with a non-isocentric approach.

The LINAC 1201 may be positioned at multiple different nodes (predefined positions at which the robot stops and radiation may be delivered) during treatment by moving the robotic arm 1202. At the nodes, the LINAC 1201 can deliver one or more radiation treatment beams to target 1220. The nodes may be arranged in an approximately spherical distribution about a patient. The particular number of nodes and the number of treatment beams applied at each node may vary as a function of the location and type of pathological anatomy to be treated. For example, the number of nodes may vary from 50 to 300, or more preferably 15 to 100 nodes and the number of beams may vary from 1100 to 3200, or more preferably 50 to 300.

Robotic arm based IGRT delivery system 1200, in accordance with one embodiment of the present invention, includes an imaging system 1210 having a processing device 1230 connected with imaging sources 1203A and 1203B (also referred to as imaging devices) and detectors 1204A and 1204B. The imaging sources 1203A-1203B may be x-ray sources, and the detectors 1204A-1204B may be x-ray detectors. The imaging sources 1203A-1203B and/or imaging detectors 1204A-1204B may have fixed positions at fixed predetermined angles. In one embodiment, the imaging sources 1203A-1203B are approximately orthogonal (e.g., have an angular separation of about 90 degrees) to facilitate stereo-imaging. Alternatively, the imaging sources 1203A, 1203B and/or imaging detectors 1204A, 1204B may be mobile, in which case they may be repositioned to maintain alignment with the target 1220.

The two imaging sources 1203A and 1203B may be mounted in fixed positions on the ceiling of an operating room and may be aligned to project x-ray imaging beams from two different angular positions (e.g., separated by 90 degrees) to intersect at a machine isocenter (referred to herein as a treatment center, which provides a reference point for positioning the patient on a treatment couch 1206 during treatment) and to illuminate imaging planes of respective detectors 1204A and 1204B after passing through the patient 1225. Imaging system 1210, thus, provides stereoscopic imaging of the target 1220 and a surrounding volume of interest (VOI).

In some embodiments, robotic arm based IGRT delivery system 1200 includes a secondary imaging system 1239. The secondary imaging system 1239 may include a rotatable gantry 1240 (e.g., a ring) attached to a robotic arm (not shown). The robotic arm may move the rotatable gantry 1240 along one or more axes (e.g., along an axis that extends from a head to a foot of the treatment couch 1206. An imaging source 1245 and a detector 1250 are mounted to the rotatable gantry 1240. The rotatable gantry 1240 may rotate 360 degrees about the axis that extends from the head to the foot of the treatment couch. Accordingly, the imaging source 1245 and detector 1250 may be positioned at numerous different angles. In one embodiment, the imaging source 1245 is an x-ray source and the detector 1250 is an x-ray detector. In one embodiment, the secondary imaging system 1239 includes two rings that are separately rotatable. The imaging source 1245 may be mounted to a first ring and the detector 1250 may be mounted to a second ring. In one embodiment, the rotatable gantry 1240 rests at a foot of the treatment couch during radiation treatment delivery to avoid collisions with the robotic arm 1202.

Detectors 1204A, 1204B, 1250 may be fabricated from a scintillating material that converts x-rays to visible light (e.g., amorphous silicon), and an array of CMOS (complementary metal oxide silicon) or CCD (charge-coupled device) imaging cells that convert the light to a digital image that can be compared with a reference image during an image registration process that transforms a coordinate system of the digital image to a coordinate system of the reference image, as is well known to the skilled artisan. The reference image may be, for example, a digitally reconstructed radiograph (DRR).

Figure 13:
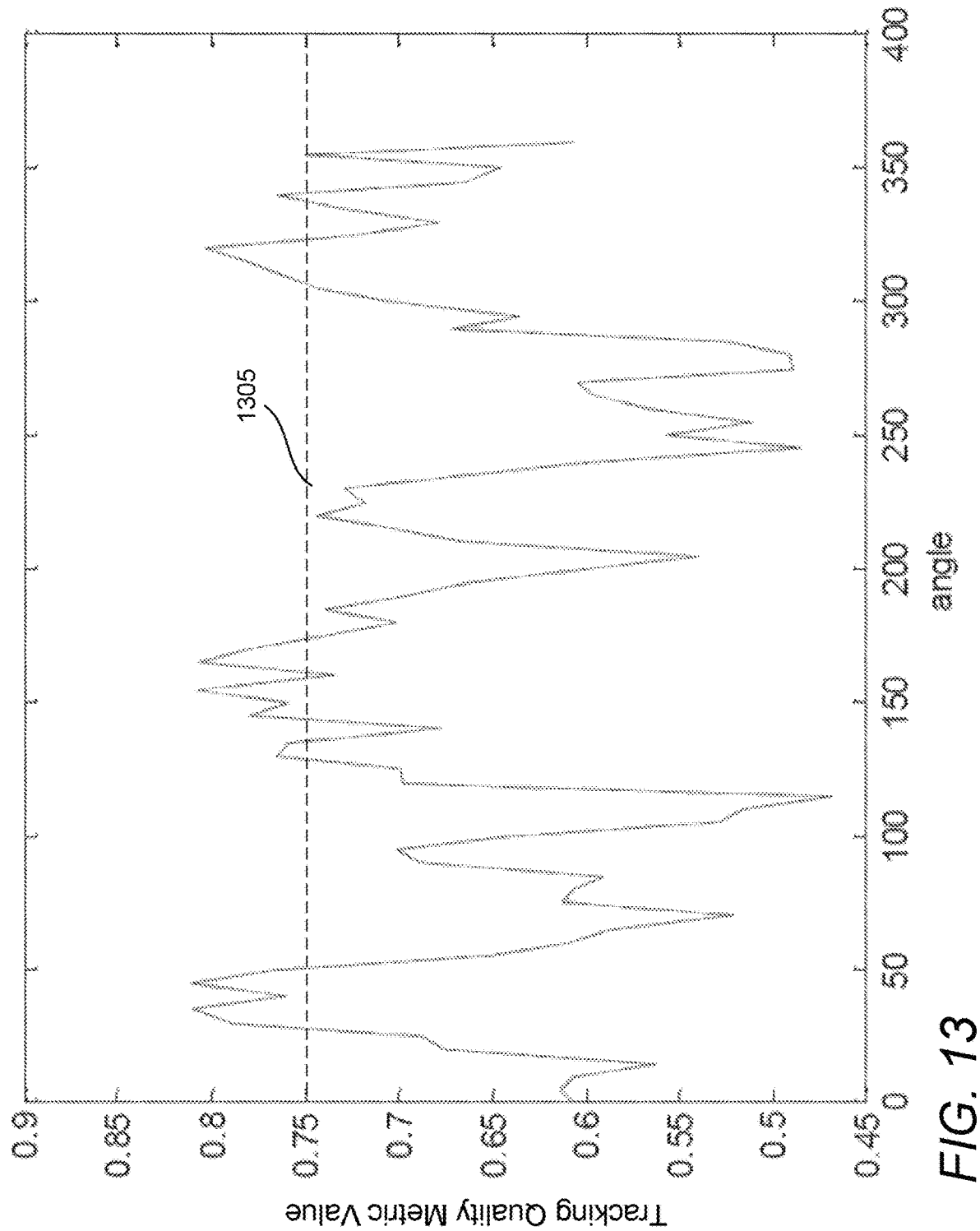
FIG. 13 illustrates example tracking quality metric values for 72 tested angles, according to a one embodiment.

FIG. 13 illustrates example tracking quality metric values for 72 tested angles, according to a one embodiment. FIG. 13 additionally illustrates an example tracking quality metric threshold. Angles having tracking quality metric values that are above the tracking quality metric threshold may be included in a set of candidate angles for use in image tracking during a treatment stage, while angles below the tracking quality metric threshold may not be included. In this example, a good candidate pair of images (each having tracking quality metric values or confidence values of over 0.8 or 80%) is 45 degrees and 135 degrees, which results in two consecutive orthogonal images.

Figure 14:
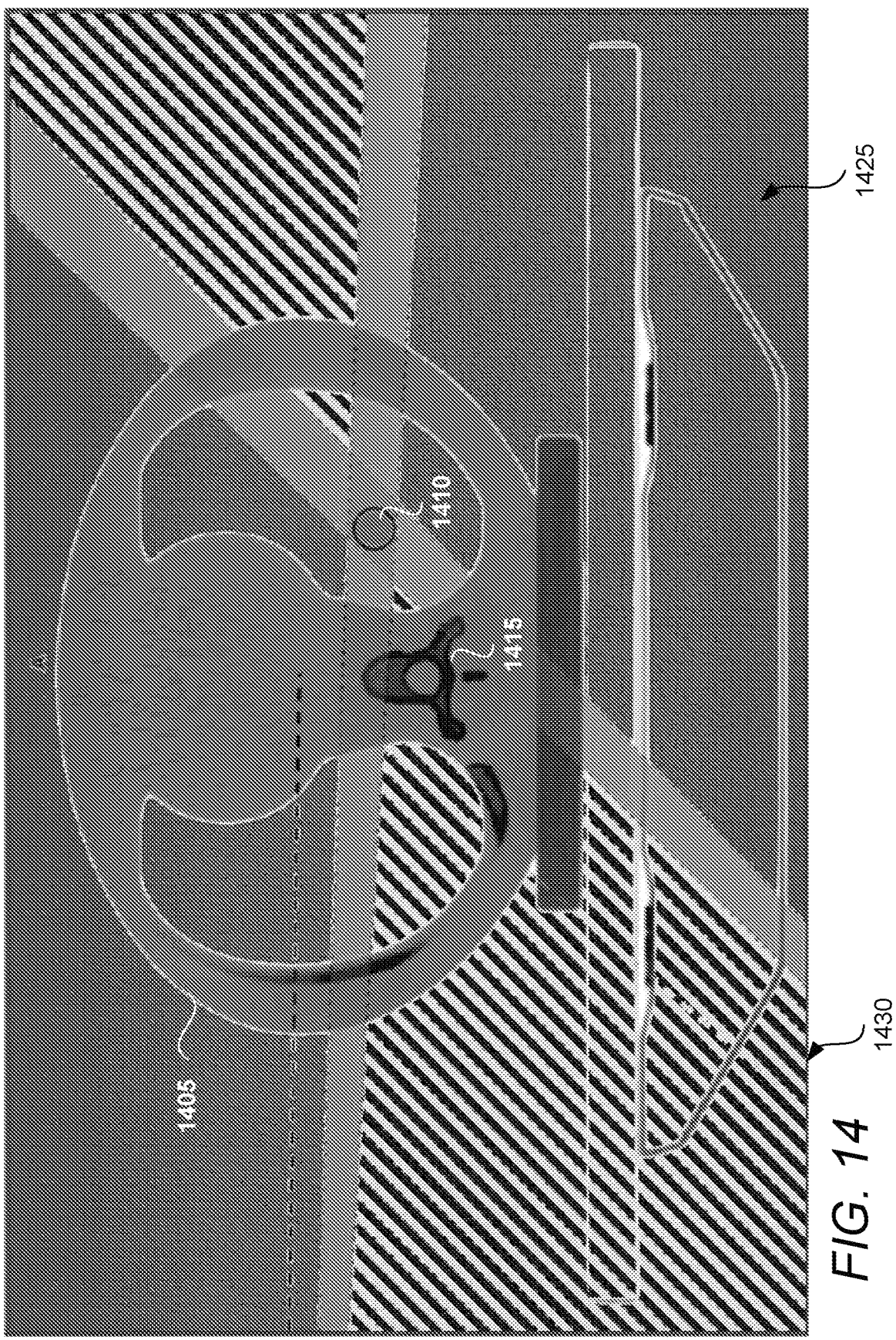
FIG. 14 illustrates an example patient along with angles that can be used to successfully track a target in the patient and angles that cannot be used to successfully track the target, according to a one embodiment.

FIG. 14 illustrates an example patient 1405 along with angles 1425 that can be used to successfully track a target 1410 in the patient and angles 1430 that cannot be used to successfully track the target 1410, according to a one embodiment. As shown, for angles 1430 the patient's spine 1415 is blocking the target 1410. Accordingly, the target 1410 may not be discernable in x-ray images taken at angles 1430. Angles 1430 cover approximately 120 degrees of rotation that should be avoided in this example. However, the spine 1415 does not overlap the target 1410 at angles 1425, and so angles 1425 may be included in a set of candidate angles for use in tracking the target 1410 during a treatment stage. Angles 1425 amount to approximately 240 degrees of rotation that are available for imaging in this example.

It will be apparent from the foregoing description that aspects of the present invention may be embodied, at least in part, in software. That is, the techniques may be carried out in a computer system or other data processing system in response to its processor, such as processing device 120 of system controller 114 and/or processing device 170 of treatment planning system 118 of FIG. 1, for example, executing sequences of instructions contained in a memory. In various embodiments, hardware circuitry may be used in combination with software instructions to implement embodiments of the present invention. Thus, the techniques are not limited to any specific combination of hardware circuitry and software. In addition, throughout this description, various functions and operations may be described as being performed by or caused by software code to simplify description. However, those skilled in the art will recognize what is meant by such expressions is that the functions result from execution of the code by a processing device such as processing device 120 or 170.

A computer-readable medium can be used to store software and data which when executed by a general purpose or special purpose processing device causes the processing device to perform various methods of the present invention. This executable software and data may be stored in various places including, for example, system memory and storage or any other device that is capable of storing software programs and/or data. Thus, a computer-readable medium includes any non-transitory mechanism that provides (i.e., stores) information in a form accessible by a machine (e.g., a computer, network device, personal digital assistant, manufacturing tool, any device with a set of one or more processors, etc.). For example, a computer-readable medium includes recordable/non-recordable media such as read only memory (ROM), random access memory (RAM), magnetic disk storage media, optical storage media, flash memory devices, etc.

Unless stated otherwise as apparent from the foregoing discussion, it will be appreciated that terms such as "determining," "computing," "generating," "comparing," "selecting," "receiving," or the like may refer to the actions and processes of a computer system, or similar electronic computing device, that manipulates and transforms data represented as physical (e.g., electronic) quantities within the computer system's registers and memories into other data similarly represented as physical quantities within the computer system's memories or registers or other such information storage or display devices. Embodiments of the methods described herein may be implemented using computer software, firmware, hardware, or a combination thereof. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

It should be noted that the methods and apparatuses described herein are not limited to use only with medical diagnostic imaging and treatment. In alternative embodiments, the methods and apparatus herein may be used in applications outside of the medical technology field, such as industrial imaging and non-destructive testing of materials. In such applications, for example, "treatment" may refer generally to the effectuation of an operation controlled by the treatment planning system, such as the application of a beam (e.g., radiation, acoustic, etc.) and "target" may refer to a non-anatomical object or area.

In the foregoing specification, embodiments of the invention have been described with reference to specific examples. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method, during a treatment stage of a target by a radiation therapy apparatus comprising a gantry that rotates at a speed of over one rotation per minute, comprising:
   selecting at least a first angle and a second angle from a set of angles for a first rotation of the gantry;
   generating, using an imaging device mounted to the gantry, a first tracking image of the target from the first angle during the first rotation of the gantry;
   generating, using the imaging device, a second tracking image of the target from the second angle during the first rotation of the gantry; and
   performing target tracking based on the first tracking image and the second tracking image.

2. The method of claim 1, wherein the first angle has a higher tracking quality metric value from the set of angles, and wherein the second angle has a separation from the first angle of at least an angle separation threshold.

3. The method of claim 1, further comprising:
   generating a third tracking image of the target from the first angle during a second rotation of the gantry;
   performing the target tracking based on the third tracking image;
   generating a fourth tracking image of the target from the second angle during the second rotation of the gantry; and
   performing the target tracking based on the fourth tracking image.

4. The method of claim 1, further comprising:
   determining that the target tracking based on the second tracking image has failed;
   continuing the treatment stage of the target;
   selecting a third angle from the set of angles;
   generating a third tracking image of the target from the third angle; and
   performing the target tracking based at least in part on the third tracking image.

5. The method of claim 4, wherein the third tracking image is generated during the first rotation of the gantry.

6. The method of claim 4, wherein the third tracking image is generated during a second rotation of the gantry.

7. The method of claim 4, wherein the third angle has a next highest tracking quality metric value after the second angle.

8. The method of claim 1, further comprising:
   determining that the target tracking based on the second tracking image has failed;
   determining a time window within which a next tracking image must be taken;
   determining that no angle from the set of angles will be available within the time window; and
   interrupting a treatment delivery for the treatment stage.

9. The method of claim 1, further comprising:
   generating a plurality of x-ray images of the target from two or more angles from the subset of the plurality of angles; and
   generating a motion model of the target from the plurality of x-ray images.

* * * * *